(12) United States Patent
Chung

(10) Patent No.: US 7,382,255 B2
(45) Date of Patent: *Jun. 3, 2008

(54) MEDICAL ASSISTANCE AND TRACKING METHOD EMPLOYING SMART TAGS

(75) Inventor: Kevin Kwong-Tai Chung, Princeton, NJ (US)

(73) Assignee: Avante International Technology, Inc., Princeton Junction, NJ (US)

( * ) Notice: Subject to any disclaimer, the term of this patent is extended or adjusted under 35 U.S.C. 154(b) by 25 days.

This patent is subject to a terminal disclaimer.

(21) Appl. No.: 11/018,646

(22) Filed: Dec. 20, 2004

(65) Prior Publication Data
US 2005/0110640 A1    May 26, 2005

Related U.S. Application Data

(63) Continuation of application No. 10/247,435, filed on Sep. 19, 2002, which is a continuation-in-part of application No. PCT/US01/42563, filed on Oct. 9, 2001.

(60) Provisional application No. 60/359,558, filed on Feb. 22, 2002, provisional application No. 60/352,901, filed on Jan. 30, 2002, provisional application No. 60/351,266, filed on Jan. 23, 2002, provisional application No. 60/341,633, filed on Dec. 19, 2001, provisional application No. 60/330,112, filed on Oct. 17, 2001, provisional application No. 60/328,661, filed on Oct. 11, 2001, provisional application No. 60/326,265, filed on Oct. 1, 2001, provisional application No. 60/323,514, filed on Sep. 19, 2001.

(51) Int. Cl.
G08B 13/14     (2006.01)
G08B 19/00     (2006.01)
H04Q 5/22      (2006.01)
G06K 5/00      (2006.01)
G06F 19/00     (2006.01)
G06F 11/30     (2006.01)
H03M 13/00     (2006.01)

(52) U.S. Cl. .................. 340/572.1; 340/5.8; 340/10.1; 235/437; 235/385; 705/3; 713/189; 714/752

(58) Field of Classification Search .. 340/572.1–572.9, 340/5.8, 10.1, 10.51, 10.52; 235/375–385, 235/437; 705/1–3, 7; 713/168, 189, 193; 714/752–785

See application file for complete search history.

(56) References Cited

U.S. PATENT DOCUMENTS 4,791,655 A    12/1988    Nagata et al.

(Continued)

FOREIGN PATENT DOCUMENTS

WO    WO 99/45498    9/1999

(Continued)

OTHER PUBLICATIONS

U.S. Appl. No. 11/701,047, filed Feb. 2007, Chung, Kevin Kwong-Tai.*

(Continued)

*Primary Examiner*—Benjamin C Lee
(74) *Attorney, Agent, or Firm*—Clement A. Berard, Esq.; Dann, Dorfman, Herrell & Skillman

(57) ABSTRACT

A medical assistance method comprises providing a coded tag that is read and compared for matching a medication, implement, medical device, treatment and/or procedure and providing an indication of a match, e.g., by a visual and/or an audible indication.

24 Claims, 14 Drawing Sheets

U.S. PATENT DOCUMENTS

| | | | |
|---|---|---|---|
| 4,931,788 A * | 6/1990 | Creswick | 340/10.33 |
| 5,051,565 A | 9/1991 | Wolfram | |
| 5,221,831 A | 6/1993 | Geiszler | |
| 5,257,011 A | 10/1993 | Beigel | |
| 5,259,025 A | 11/1993 | Monroe et al. | |
| 5,272,318 A | 12/1993 | Gorman | |
| 5,291,411 A | 3/1994 | Bianco | |
| 5,396,218 A | 3/1995 | Olah | |
| 5,401,944 A | 3/1995 | Bravman et al. | |
| 5,412,727 A | 5/1995 | Drexler et al. | |
| 5,465,082 A | 11/1995 | Chaco | |
| 5,627,517 A | 5/1997 | Theimer et al. | |
| 5,650,768 A | 7/1997 | Eswaran | |
| 5,661,470 A | 8/1997 | Karr | |
| 5,682,142 A | 10/1997 | Loosmore et al. | |
| 5,732,401 A * | 3/1998 | Conway | 705/29 |
| 5,845,264 A * | 12/1998 | Nellhaus | 705/28 |
| 5,886,634 A | 3/1999 | Muhme | |
| 5,887,176 A | 3/1999 | Griffith et al. | |
| 5,914,671 A | 6/1999 | Tuttle | |
| 5,917,174 A | 6/1999 | Moore et al. | |
| 5,936,527 A | 8/1999 | Isaacman et al. | |
| 5,963,136 A | 10/1999 | O'Brien | |
| 5,971,279 A | 10/1999 | Raistrick et al. | |
| 5,979,941 A * | 11/1999 | Mosher et al. | 283/67 |
| 6,002,344 A | 12/1999 | Bandy et al. | |
| 6,100,804 A | 8/2000 | Brady et al. | |
| 6,111,506 A | 8/2000 | Yap et al. | |
| 6,139,495 A * | 10/2000 | De La Huerga | 600/300 |
| 6,150,942 A | 11/2000 | O'Brien | |
| 6,232,877 B1 | 5/2001 | Ashwin | |
| 6,255,951 B1 * | 7/2001 | De La Huerga | 340/573.1 |
| 6,294,999 B1 | 9/2001 | Yarin et al. | |
| 6,397,190 B1 | 5/2002 | Goetz | |
| 6,421,013 B1 | 7/2002 | Chung | |
| 6,427,913 B1 | 8/2002 | Maloney | |
| 6,574,166 B2 | 6/2003 | Niemiec | |
| 6,657,543 B1 * | 12/2003 | Chung | 340/573.1 |
| 6,671,563 B1 * | 12/2003 | Engelson et al. | 700/2 |
| 6,720,865 B1 | 4/2004 | Forster et al. | |
| 6,883,710 B2 * | 4/2005 | Chung | 235/385 |
| 6,961,000 B2 * | 11/2005 | Chung | 340/572.1 |
| 7,098,793 B2 * | 8/2006 | Chung | 340/572.1 |
| 7,158,030 B2 * | 1/2007 | Chung | 340/572.1 |
| 2001/0028308 A1 | 10/2001 | De La Huerga | |

FOREIGN PATENT DOCUMENTS

WO    WO 01/54055    7/2001

OTHER PUBLICATIONS

U.S. Appl. No. 11/414,916, filed May 2006, Chung, Kevin Kwong-Tai.*

En-Vision America, "Welcome to our Homepage", en-Vision America—Specializing in assistive technology products for Low Vision and Blindness. Indep . . . http://www.envisionamerica.com/grindes.html, 14 Pages.

PCT International Preliminary Examination Report, Mar. 11, 2004, 10 Pages.

* cited by examiner

FIGURE 13A
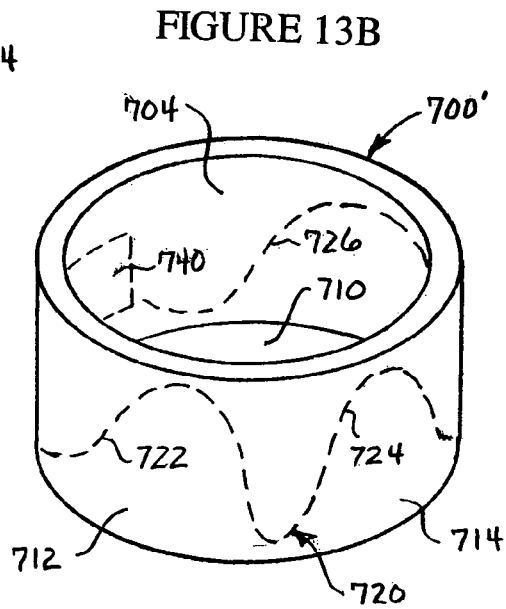
FIGURE 13B
FIGURE 13C
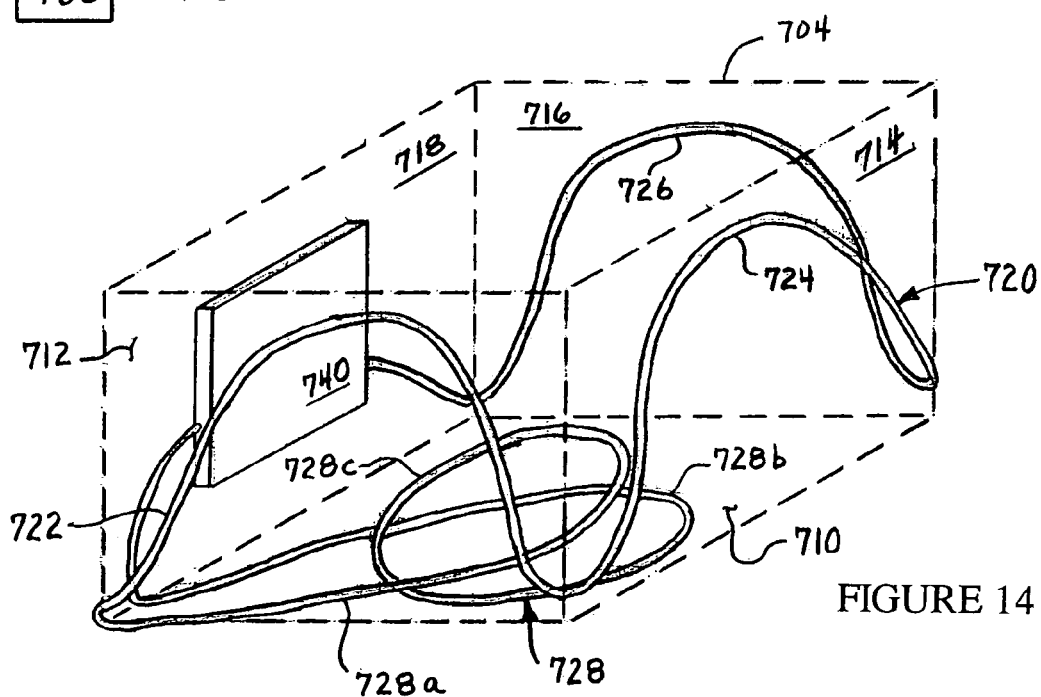
FIGURE 14

MEDICAL ASSISTANCE AND TRACKING METHOD EMPLOYING SMART TAGS

This Application is a continuation of U.S. patent application Ser. No. 10/247,435 filed Sep. 19, 2002, which is a continuation in part of PCT Application No. PCT/US01/42563 filed Oct. 9, 2001, and which claims the priority thereof, and which further claims the benefit of:

U.S. Provisional Application Ser. No. 60/323,514 filed Sep. 19, 2001,
U.S. Provisional Application Ser. No. 60/326,265 filed Oct. 1, 2001,
U.S. Provisional Application Ser. No. 60/328,661 filed Oct. 11, 2001,
U.S. Provisional Application Ser. No. 60/330,112 filed Oct. 17, 2001,
U.S. Provisional Application Ser. No. 60/341,633 filed Dec. 19, 2001,
U.S. Provisional Application Ser. No. 60/351,266 filed Jan. 23, 2002,
U.S. Provisional Application Ser. No. 60/352,901 filed Jan. 30, 2002, and
U.S. Provisional Application Ser. No. 60/359,558 filed Feb. 22, 2002.

The present invention relates to a medical method, and in particular, to a method employing a coded tag for assisting with or reducing error in any one or more of administering a medication, using an implement, using a medical device, administering a treatment and performing a procedure.

Typically, shipping and/or receiving and/or dispensing and/or using articles utilizes paper documents such as prescriptions, medical orders, bills of lading and manifests and/or paper labels that relate the objects being shipped or transported to their owner or to the designated or authorized recipient. Such documents and labels often include a bar code for automatic reading by an optical scanner that is in line-of-sight communication with the bar code. In such operations there is usually a desire to maintain a complete, accurate and up to date record of the objects shipped and received. Automated or automatic methods of providing such record are desirable, however, conventional methods all have shortcomings that result in less than the desired tracking and record being provided.

Labels applied to the objects were an attempt to afford relative automated record keeping, but tended to be cumbersome to use and error prone. More sophisticated automatic methods employed bar-coded labels and/or magnetic stripe tags, each with suitable readers. While the cost of such labels and cards is low, so is the information that can be embedded or coded in either of these media, even where complex bar codes such as a 2-D bar code is employed. In addition, most bar code readers are read-only devices that can only read the information stored in the bar code or magnetic stripe and cannot store any additional information in the bar-code label or magnetic stripe card. In addition, bar codes and magnetic stripes cannot store sufficient information to provide the desirable features necessary without a connection to a central computer and online information system Moreover, bar-code media require a "line-of-sight" communication path between device and reader, and magnetic stripe media require a direct or close contact communication path between device and reader at a suitable "swiping speed," and the reliability of correct reading is about 80-90%, as anyone who has gone through a store check-out bar-code reader or a magnetic stripe credit card reader will recognize. Repeated passes of the object in front of the bar-code reader or swipes of the card reader create delay and annoyance and/or can produce record errors. Such problems are not overcome with more complex bar codes, and could be exacerbated where the bar code elements are smaller in size and thus more sensitive to smudging and dirt.

Electronic tracking using radio frequency identification (RFID) tags is one way to overcome the disadvantages of the prior art bar-code and magnetic stripe approaches. Prior art systems typically do not track the articles to be tracked along the processing path and/or do not have reliable, essentially 100% correct reader performance, essentially without the need for human intervention, as is desirable for providing complete and accurate records.

In a medical environment, errors in the dispensing, administration and prescribing of medications and medical treatments have resulted in an unacceptably large number of adverse reactions, including many deaths and permanent impairments and disability. Various estimates of the consequences thereof include tens of thousands of patients affected and annual costs exceeding $3-billion U.S. dollars. Published material reports 770,000 injuries caused by medication errors over a two-year period and an estimated 44,000 to 98,000 fatal incidences arising therefrom with a total cost of $177 billion for hospital care and long-term care. The costs created by counterfeit drugs that are ineffective, contain no or incorrect active ingredients, or the incorrect amounts or proportions of active ingredients make the problem worse.

Bar-coded labels and magnetic stripe cards have not proved completely satisfactory due to the need for line-of-sight readers and significantly less than 100% reading rate. Moreover, absent a network connection to a computer, the known prior art arrangements do little more than to read the information stored in the bar code or magnetic stripe, and cannot detect errors therein, which is a particular disadvantage in relation to medication and medical devices wherein errors in dispensing and/or using the medication or device can have serious, if not fatal, consequences.

The special needs of the elderly, infirm, hearing impaired and visually impaired persons is not addressed by the prior art devices. The Healthcare Insurance Portability and Accountability Act adopted in 1996 seeks to address certain aspects of this problem Prior art devices do not address these needs, and are too costly to permit home use, e.g., for providing automatic reminders to take medication and/or to give warning when medication is taken improperly in time and/or amount.

Accordingly, there is a need for apparatus and method that can assist in the dispensing and administration of medication and/or medical treatment. Desirably, such should facilitate tracking an object at various stations and associating the object with a desired recipient. It would be advantageous if the method and system has a high correct-reading ability (e.g., near 100%), and does not require line-of-sight readers. It would also be desirable that the method and apparatus be suitable for use in a home setting, e.g., by a consumer or patient, as well as in a professional or commercial setting, e.g., in a pharmacy, hospital, nursing home or other care-giving facility.

To this end, the method of the present invention comprises providing a coded tag, reading the coded tag, comparing read data for matching a medication, implement, medical device, treatment and/or procedure, and providing an indication based thereon, e.g., by a visual and/or an audible indication.

BRIEF DESCRIPTION OF THE DRAWING

The detailed description of the preferred embodiments of the present invention will be more easily and better understood when read in conjunction with the FIGURES of the Drawing which include:

FIGS. 13A and 13B are isometric views of example embodiments of an open antenna array and FIG. 13C is a view of the bottom of the example antenna array of FIG. 13A; and FIG. 14 is an isometric diagram illustrating the arrangement of the antenna of the example antenna array of FIGS. 13A and 13C.

Figure 1:
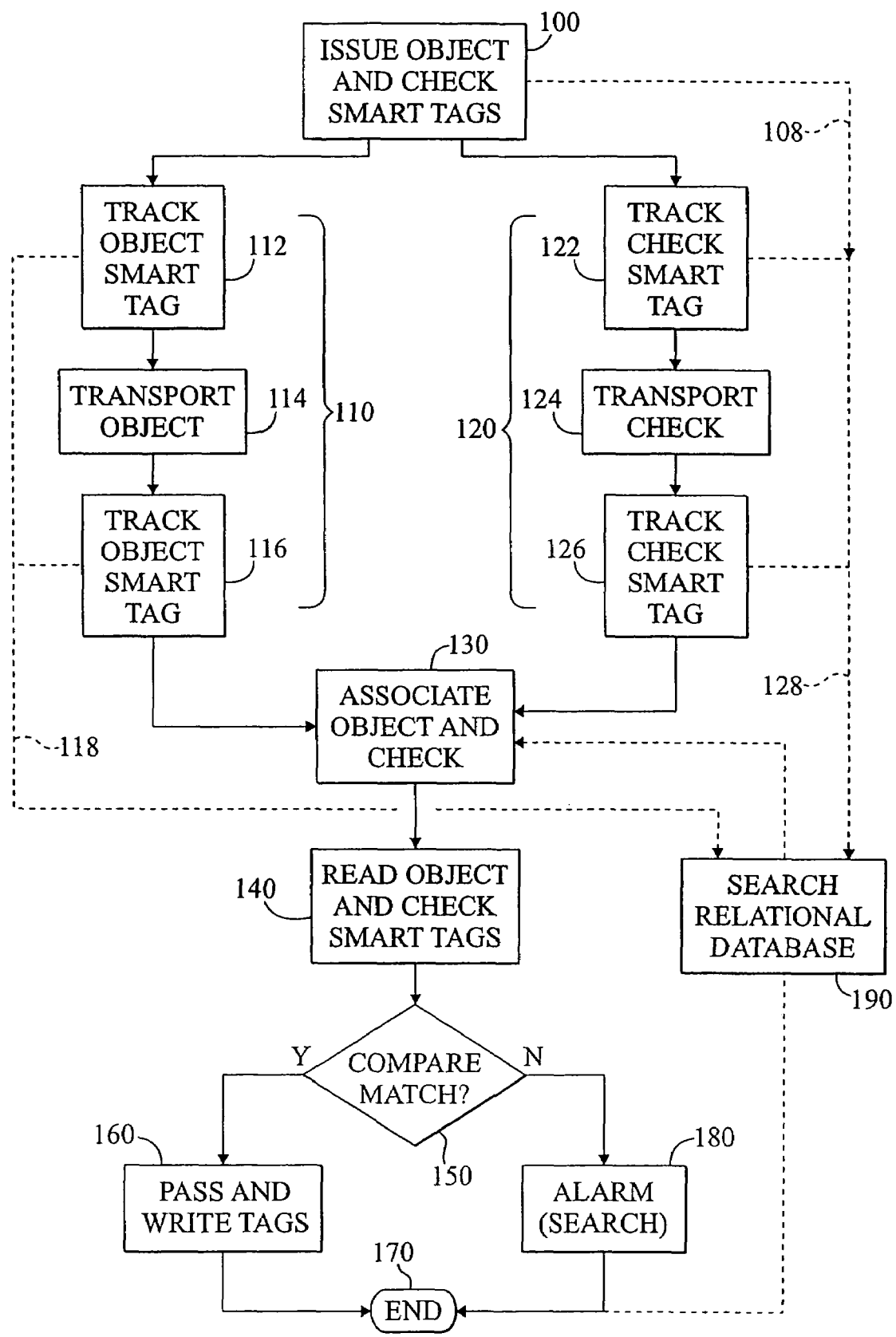
FIG. 1 is a flow chart schematic block diagram illustrating an example embodiment of a tracking system and method.

In the Drawing, where an element or feature is shown in more than one drawing figure, the same alphanumeric designation may be used to designate such element or feature in each figure, and where a closely related or modified element is shown in a figure, the same alphanumerical designation primed may be used to designate the modified element or feature. Similar elements may be shown in the same figure designated by different "dash numbers" such as X-1, X-2, and so on. It is noted that, according to common practice, the various features of the drawing are not to scale, and the dimensions of the various features are arbitrarily expanded or reduced for clarity.

DESCRIPTION OF THE PREFERRED EMBODIMENT(S)

In general, a system and method is useful for tracking an article or object at one or more stations over a transport path and associating the article or object with a recipient or another object. A smart tag is associated with each article to be tracked, for example, by being attached to the article either directly or indirectly, e.g., to a container containing the article. A second smart tag is associated with the recipient or other object with which the first object is to be associated after passing along the transport path. Each smart tag includes at least an electronic memory coupled to an antenna by which information from the memory may be transmitted and/or information may be received and stored in the memory. Smart tag control units (readers and/or writers) and antenna arrays at various stations communicate with the smart tags and may also communicate directly or indirectly with one or more processors that process the information, for example, for monitoring and/or controlling the stations and/or control units and/or lines including one or more stations.

As used herein, the following terms are used to include but are not limited to:

"Article" and "object" and "person" are used interchangeably to refer to any article, object or other thing or person or animal to which a smart tag may be attached or with which a smart tag may be associated. Examples include, but are not limited to, packages, parcels, containers, medications, medical devices, instruments, implements, containers therefor and the like in a medical or hospital environment. A person may be an "object" in, for example, a medical environment where the apparatus and/or method is utilized for associating a person as patient with his medication, medical device, treatment and/or other procedure.

"Electronic gate" is used to refer to an antenna or array of antenna in combination with a smart tag reader/writer that communicates with a smart tag via the antenna or array, and which may also include a display, annunciator or other device for providing information in human perceivable form The antenna or antenna array may be disposed at an entry point or other location of a station for receiving information produced from a smart tag that is within its detection region and for transmitting information to be stored in the memory of a smart tag within its detection region, or at a point of use or treatment or other location.

"Smart tag" and/or "wireless tag" and/or "RFID tag" is used to refer to an article that includes at least an electronic memory wherein information from the memory may be transmitted and/or information may be received and stored in the memory. A "wireless" type smart tag including an antenna is preferred, wherein the information is electromagnetically coupled from or to the antenna over a distance or range. However, a "contact" type smart tag, wherein the information is electrically coupled through physical electrical connections made to contacts on the smart tag, may also be utilized, although it is less convenient.

"Station" is used to refer to any dispensing location, treatment location, point of use, booth, station, gate, portal, check-in position, article claim, check point, manufacturing or processing location, ramp, conveyor, conveyance, shipping area, receiving area, and the like that one or more objects may be at or pass at which a smart tag may be issued, read, written to, and/or collected.

"Transport path" is used to refer to any path, route, conveyor, conveyance, carriage or other means or combination of means by which an object, article or person may move or be moved from one place to another. FIG. 1 is a flow chart schematic block diagram illustrating an example embodiment of a tracking method. The process illustrated is described in general terms and then is described in terms of examples of various utilizations thereof, such as medication and/or medical device and/or implement tracking in a medical environment.

For simplicity, the apparatus and/or method are described in terms of one or more smart tags (e.g., two smart tags) associated respectively with one or more objects (e.g., two objects), although any number of smart tags and/or objects may be associated and tracked individually and/or as a set or group. E.g., one patient may receive one or more medications and/or medical devices, and/or may receive medication and/or medical device at one or more times.

The process of FIG. 1 commences with the issuing 100 of one or more smart tags coded with related information, typically two smart tags where a tracked object is to move over a transport path that differs in some respect from the transport path over which a check object moves, and/or is to be verified or checked at one or more locations thereof and/or at a terminus thereof. Typically, the tracked object and the checked object are associated at the beginning of the transport path, such as by being in the same location or origin, or by being in possession of one person, and are to be again associated at the end of the transport path, such as at a dispensing location, point of use, pick-up location, collection point or other destination. The smart tag issued to be attached to or associated with the tracked object is referred to as the object smart tag and the smart tag to be associated with the check object is referred to as the check smart tag.

In a hospital, clinic, pharmacy, nursing home or other medical facility or environment, the tracked object may be medication, medicine, a medical device and/or implement and the like, and the check object may be a prescription, written order, patient chart and/or patient identification band and the like.

The information stored in the memory of each smart tag when issued 100 may include any one or more of the identity of the tag, the object, the patient, medication, dosage and frequency, use instruction, expiration, refills, the physician and/or dispenser, the owner and/or sender and/or recipient, the origin and/or destination, the route, routing and/or other transport path information, the carrier(s), date and time information, issuing location and personnel, and/or any other desired or useful information. Such information is written into the memory of each smart tag as is an identifier associating each of the plural smart tags relating to a particular object or set of objects with the other or others. The smart tags will typically be flexible so that they can easily conform to a label or tag or paper receipt to which they are attached, e.g., adhesively.

The tracked object is tracked 112, 116 by reading the smart tag associated with it as it is transported 114 over transport path 110. For example, the tracked object is tracked 112 as it begins being transported 114 and is tracked 116 as it completes being transported and is to be associated 130 with the checked object. Steps 112-116 may represent the transport path 110 or one segment of a plural segment transport path 110 indicated by the dashed portion of the arrow emanating from box 116. Any number of transport segments 114 and tracking points 112, 116 may be utilized along the transport path 110.

The check object is tracked 122, 126 by reading the check smart tag associated with it as it is transported 124 over transport path 120. For example, the check object is tracked 122 as it begins being transported 124 and is tracked 126 as it completes being transported and is to be associated 130 with the tracked object. Steps 122-126 may represent the transport path 120 or one segment of a plural segment transport path 120 indicated by the dashed portion of the arrow emanating from box 126. Any number of transport segments 124 and tracking points 122, 126 may be utilized along the transport path 120.

Tracking and monitoring movement of the object smart tags and check smart tags may be accomplished in several different ways. Each tracking 112, 116, 122, 126 may include, in addition to reading information from the smart tag, the writing of tracking information to the smart tag so that as the smart tag moves along the transport path it accumulates information identifying the tracking 112, 116, 122, 126 electronic gates it passes and the date and time thereof. Tracking information may include, for example, the identity of each tracking station passed and the date and time thereof. Thus, each smart tag has the history of its travel stored in its memory, which tracking information can be read should the object and its smart tag not be in the expected destination when expected.

Alternatively and/or additionally, and optionally, such tracking information can be communicated along with smart tag identifying information to a processor and stored in a relational database for easy and quick reference and access as needed or desired, as described below. Further, and also alternatively and/or additionally, and optionally, such tracking information and tag identity information can be stored in the smart tag reader associated with each electronic gate at which tracking 112, 116, 122, 126 occurs, for later retrieval, as and/or if needed.

The tracked object and the checked object are associated 130 at the end of their respective transport paths 110, 120 and the object and check smart tags associated with the tracked object and the check object, respectively, are read 140. The information read 140 from the two smart tags is compared 150 to determine whether they match 150, i.e. whether the object smart tag and the check smart tag were issued 100 together containing the proper relating information that was written therein at issuing 100.

If a match 150 is found (path "Y"), the tracked and checked objects pass 160 from the tracking process which ends 170. The object smart tag and check smart tag may go with the objects, preferably with the writing 160 of information to the smart tags indicating that they have been matched with the objects to be matched or erasing the information stored in the smart tags that relates to the objects being tracked. One or both of the object and check smart tags may be collected, and so are available to be erased and reused, and are unavailable for unauthorized attempts at reuse.

If a match 150 is not found (path "N"), as will occur if only one of the object and check smart tags is present without a properly matched companion tag, or if the object and check smart tags present do not contain proper relating information, or if an additional unrelated smart tag is present. In these cases, an alarm 180 may be given by any suitable means, such as a light, audible signal, signal to an official or police, or combination thereof, and the process ends 170.

Alternatively and/or additionally, and optionally, if a match 150 is not found, a search 180 is initiated for the missing one of the object smart tag or the check smart tag relating to the smart tag that was read 140. A search 190 is preferably conducted by identifying the records of a relational data base that includes a record for each smart tag each time it is read at any one or more of the electronic gates. Issuing 100 and tracking 112, 116 of object smart tags and tracking 122, 126 of check smart tags both include reading and/or writing of information to and/or from the memory of the smart tag and communicating 118, 128 such read and/or written information to a relational database running on a processor. As smart tags are issued 100 and tracked (read) 112, 116, 122, 126, 140, records are accumulated in the relational database that provide a chronology and history of the transport of both object and check smart tags so that their most recent location and complete travel history are readily available.

Considering FIG. 1 in the environment of a medical facility, such as a hospital and/or pharmacy, for example, wherein medication and/or medical device, supplies and implements are issued 100 for a particular patient, procedure or use: Dual smart tags are issued 100 for each procedure, treatment, medication and/or medical device ordered. One smart tag, an object smart tag, is issued 100 for each medication, medical device, implement, procedure and/or treatment and is affixed to the container therefor in the pharmacy, the implement to be utilized or the facility, such as the surgical operating room, diagnostic machine and the like, to be utilized. Where the medication, medical device or implement, for example, has plural units packed or contained in a larger unit or container, object smart tags are issued and affixed to each of the plural units.

The object smart tag is encoded to contain, for example, a Ser. No. or other smart tag identifier, the identity of the medication and/or medical device, quantity and dosage, frequency and conditions of use, manufacturer and/or provider, expiration date, and the identity and particulars of the implement, procedure and/or treatment with which the object smart tag is associated or affixed. A paper label containing the same information as is stored in the object smart tag may also be issued and affixed to or associated with the medication, medical device, implement, procedure and/or treatment.

When a doctor, physician or other personnel writes a prescription, referral, script or other order for medication and/or medical device, a procedure and/or treatment, he utilizes a device that issues a check smart tag that is affixed to an otherwise conventional paper document. Encoded in the check smart tag is information such as, for example, a Ser. No. or other smart tag identifier, the identity of the medication, medical device, implement, procedure and/or treatment, dosage, form and frequency of administration information, refill and repetition information, issue and/or expiration dates, the patient's name and other patient information, the name of the physician or other person writing the order, and/or the diagnosis or sickness or condition. The paper document preferably contains the same information in human-readable form.

The medication, medical device, implement, procedure and/or treatment with the object smart tag associated or affixed is transported 114 over transport path 110 to the destination, i.e. the point at which the medication, medical device, implement, procedure and/or treatment associated with the object smart tag is administered or used. Along transport path 110, the object smart tag is read and tracked 112, 116. The patient and order with check smart tag affixed is transported 124 over transport path 120 to the destination, i.e. the point at which the medication, medical device, implement, procedure and/or treatment associated with the check smart tag is administered or used. Along transport path 120, the check smart tag is read and tracked 122, 126.

At the destination, the patient and his check smart tag are associated 130 with the medication, medical device, implement, procedure and/or treatment and its object smart tag, and both object and check smart tags are read 140 and compared 150 to determine whether they match. If there is a match 150 ("Y"), then the proper medication, medical device, implement, procedure and/or treatment is present for that patient as ordered, and the administration or conduct thereof may proceed 160. If there is no match 150 ("N"), an alarm 180 is given and the patient is not administered the unordered or otherwise incorrect medication, medical device, procedure and/or treatment is not administered, and the wrong implement is not utilized.

In the case of no match 150 ("N"), a search 190 may be conducted to identify and associate with the patient the proper medication, medical device, implement, procedure and/or treatment, all of which are tracked in a relational database. Alternatively and/or additionally, and optionally, search 190 may be conducted for each reading 140 of the object and check smart tags for associating related information from the relational database. Such additional information may include, for example, the patient's other medical conditions and medications, medical conditions, allergies and reactions, drug interactions, the effectiveness of the prescribed medication and/or medical device or treatment for the indicated illness, disease or condition, and the like, and is utilized to alarm or alert 180 personnel as to any actual or potential problem or adverse effect.

It is noted that the transport paths 110, 120 may be entirely or partially within a given facility, such as a pharmacy or hospital. In such case, the pharmacist receives the prescription or order with the check smart tag affixed and a tag reader reads 112 the information therein to provide a "pick-list" of the medications, devices and implements ordered, and can print the prescription labels therefor. The medication and/or medical device and/or implement filling the prescription has an object smart tag affixed thereto is associated 130 with the prescription having a check smart tag affixed thereto, and is dispensed at a window or "tunnel" or other dispensing point that includes an antenna and smart tag reader for reading 140 both the object and check smart tags and comparing 150 same for a match, as described. At this time, the pharmacist or other dispenser is alerted to any error or problem determined from the comparing 150 and/or from searching 190 the relational data base and/or medical information database. On the other hand, parts of transport paths 110, 120 may also be in different facilities and locations.

For example, where the disease or condition is encoded in the check smart tag, and the relational database includes or is linked to a medical information database that includes medication and/or medical device, treatment and effectiveness information, then medical personnel are provided an indication of whether that prescribed is a functionally useful treatment such as a specific medication, or is useful as a supplement such as a vitamin or mineral or herb, or is functionally neutral or is functionally adverse or contraindicated. Such databases of medications and/or treatments are available and may be linked to the relational database utilized for searching 190 object and check smart tag records. One such database is available from eProcrates located in San Diego, Calif.

A significant advantage of such arrangement is the reduction of mis-prescribing and inappropriate and/or unnecessary treatment, or other human-errors due to an alarm or alert being provided. Likewise, drug interactions, adverse reactions and allergies are avoided. It is noted that such medical relational database can be coupled to the smart tag issuing 100 so that the physician or other person ordering medication and/or medical device or treatment is alerted to any potential problems at an early time.

In addition, at reading 140 just prior to dispensing 160, the patient information from the check smart tag may be written 140 to the object smart tag on the medication and/or medical device or implement, and the object smart tag may thereafter be utilized with another smart tag reader described below to provide, for example, patient warnings and reminders, either visually or audibly, for alerting the patient to take the medication and/or to have a prescription refilled, or at the patient's home, living place or other point of use.

Thus it is evident that the same system elements may be configured to provide an apparatus and/or method in any one of many types of environments, facilities, locations, functions and operations. One example thereof is a facility, typically a centralized facility, at which large numbers of prescriptions for medicine, medical devices and the like are ordered via telephone and/or computer and are then filled and are dispensed via the mail or a delivery service. Typically such facility is operated by a pharmaceutical company or distributor contracting with a health insurance provider for providing medication and/or devices for treating long term and/or chronic conditions.

Figure 2:
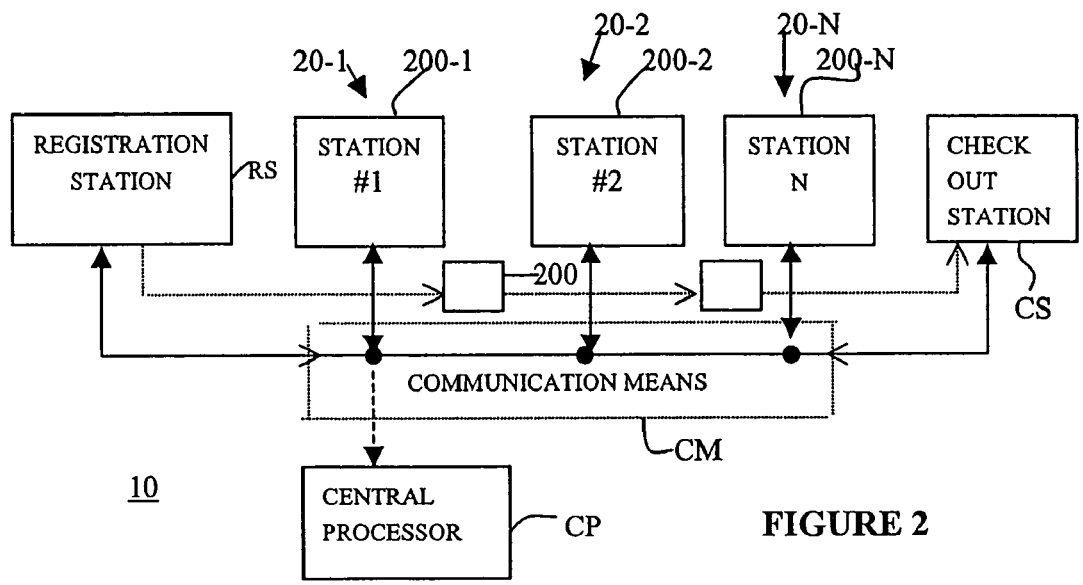
FIG. 2 is a schematic block diagram illustrating an example of a system including plural stations.

FIG. 2 is a schematic block diagram illustrating an example of a system 10 including plural stations 20-2, 20-2, . . . 20-N. Check in and registration station RS is for receiving information relating to the object to be tracked and the check object, and coding that information into the memory of plural smart tags 200 that are issued accompany the tracked object and the check object. Typically, smart tags 200 are issued as part of an identification label or claim check displaying the pertinent information in human readable form. Station RS is monitored by processor CP and communicates the information stored in smart tags 200 thereto, and may be under the control of processor CP. Similarly, stations 20-1-20-N and check-out station CS also communicate with and may be controlled by processor CP.

Because the object smart tags and check smart tags are the same functionally except for the information stored therein, and the various stations (electronic gates) are the same functionally, the system operates with both object and check smart tags in the same manner, i.e. reading and writing data from and to the smart tags 200 at each tracking station 20-1-20-N that the particular tags pass. Thus, FIG. 2 illustrates a smart tag 200 traveling over transport path TP which can be either an object smart tag or a check smart tag.

As the issued object smart tag 200 attached to the tracked object moves over its transport path TP past ones of the various tracking stations 20-1 through 20-N, object smart tag 200 is read by the respective electronic gate at each station 20 passed. The information so read from the object smart tag 200 may be stored in a memory of the electronic gate of station 20 and/or may be communicated to a central computer or processor CP via any suitable communication link. Information relating to the object and object smart tag 200 passing each tracking station 20, such as the identity of the station and the date and time of passing, is either stored in (written to the memory of) object smart tag 200 and/or is stored in the electronic gate and/or is communicated to the central computer CP, for later retrieval and use.

Separately, as the issued check smart tag 200 attached to the object moves over its transport path TP past ones of the various tracking stations 20-1 through 20-N, check smart tag 200 is read by the respective electronic gate at each station 20 passed. The information so read from the check smart tag 200 may be stored in a memory of the electronic gate of station 20 and/or may be communicated to a central computer or processor CP via any suitable communication link. Information relating to the check and check smart tag 200 passing each tracking station 20, such as the identity of the station and the date and time of passing, is either stored in (written to the memory of) check smart tag 200 and/or is stored in the electronic gate and/or is communicated to the central computer CP, for later retrieval and use.

When the object and object smart tag 200 has completed its travel over its transport path TP to reach the destination, having passed those of tracking stations 20-1 through 20-N that are along transport path TP, it becomes associated with the check and check smart tag 200. Check and check smart tag 200 has completed its travel over its transport path TP to reach the destination, having passed those of tracking stations 20-1 through 20-N that are along its transport path TP. Check out station CS then reads the object smart tag 200 and the check smart tag 200 and compares the information therefrom for a match to indicate that the proper object and check have been associated at the destination.

Where an object and check do not become properly associated at a destination, one or the other is at the wrong destination, and a search can be conducted by processor CP relating the records of the relational database therein pertaining to the particular object smart tag 200 or check smart tag 200 that is at the destination. Because both object and check smart tags 200 are preferably tracked and tracking information is stored in the relational database of processor CP, the whereabouts and travel of either or both may be quickly ascertained. If desired check out station CS may provide a tangible record of such information to any desire degree of detail. For example, a simple form of such tangible record may include the missing object's or missing check's identification and a list of tracking stations by which it passed. A more comprehensive form of the tangible record may include the object's identification, a list of the tracking stations passed, a list of the dates and times thereof, information about the object, its owner, the shipper or recipient, and any other data stored in the relational database of processor CP.

Moreover, such tangible record may be any one or more of a printed document, a computer floppy disk, a computer CD-ROM disk, or any other desired medium. Where the tangible record is a computer readable medium, such as a floppy disk or a CD-ROM disk, the medium, the computer readable files thereon may include files directing access to either a central web site or to particular web sites at which further information may be accessed and/or retrieved. Such record may be provided to personnel seeking to find and match up the missing object or check or to the owner, shipper or recipient thereof, or other person, as may be desirable and appropriate.

While only one processor (computer) is necessary to the system 10, it is often convenient to employ a network of processors (computers) in which plural de-centralized processors are linked, as by a network, for example, together and/or to a central processor CP. Typically, each local processor is associated with one or more stations 20 for monitoring the operation thereof and/or for controlling such station(s) 20, and is linked with the central processor CP for communicating monitoring information therewith and/or for communicating control and/or programming information therewith Thus, stations 20 may operate independently, under the control of local computer, under control of central computer CP, or some combination thereof.

Communication between the registration station RS, the various tracking stations 20-1 through 20-N, checkout station CS and (local processors and) central processor CP may be via any suitable communication means CM including but not limited to wire, cable, optical fiber, local area network (LAN), wide area network (WAN), radio (RF) transmission, optical transmission or other suitable means, or any combination thereof, with or without one or more communication hubs. Such communication may be in real time, be periodic or aperiodic, and may include one or more communications, and may utilize any suitable format or protocol, such as the RS485 and/or RS232 standards.

Communication may occur periodically, but promptly (e.g., within seconds or minutes) relative to the speed and frequency of passing of the objects in transport and the time and date thereof, and the timeliness of tracking and monitoring desired. Communication may be periodic, but less frequent, regarding the status of a station 20. Periodic communication may be beneficial for wireless communication to reduce frequency spectrum and bandwidth requirements, and communication units may be placed at higher locations and unobstructed positions, such as in a tall building, or other suitable location for proper communication.

Suitable communication devices are available commercially from several sources and provide direct communication or communication via relay links. Such devices are suitable for communication between computers over local area and wide area networks and may employ CDMA and/or spread spectrum communication techniques. For example, RF communication devices available from Proxim, Inc., located in Sunnyvale, Calif., include, for example, a Range-LAN2 system operating at 2.4 GHZ, a Stratum Building-to-Building system, and a Symphony Home and Small Office system. Such devices transmit and receive information and programming changes between and among central processor CP and local computers and/or control units 40 equipped with a compatible communication device.

Where information is written to and stored in smart tag 200 at each of tracking stations 20-1 through 20-N, communication may be by check out station CS reading the information so stored in smart tag 200. Smart tag 200 may be collected by check out station CS, thereby permitting reuse of the smart tags 200.

Figure 3:
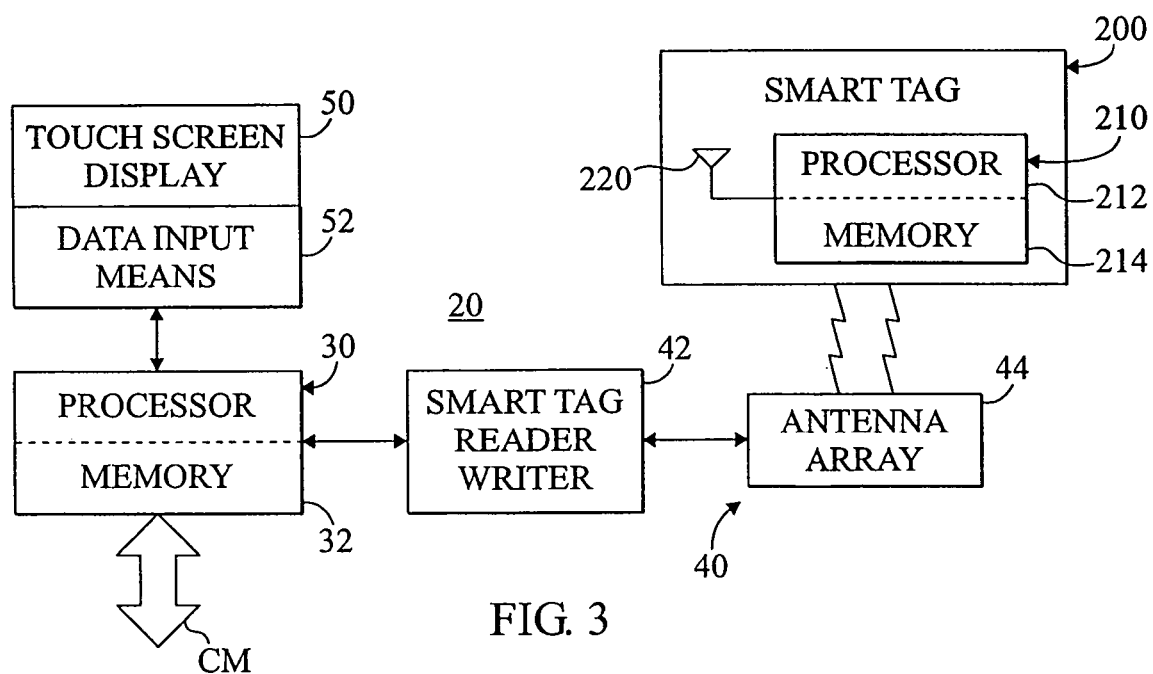
FIG. 3 is a schematic block diagram of an example of a tracking station useful in the system of FIG. 2.

FIG. 3 is a schematic block diagram of an example of a tracking station 20 useful in the system of FIG. 2. Station 20 includes an electronic gate 40 and a processor 30 for communicating with smart tag 200, which may be an object smart tag or a check smart tag. Processor 30 is coupled to electronic gate 40 which includes a smart tag reader and/or writer 42 for at least receiving and decoding information from a smart tag 200 that is within its detection region. Processor 30 includes one or more memory devices for storing information relating to station 20, date and time, and the like, and for storing information read from a smart tag 200 or entered via optional data input means 52. Information from memory 32 is produced and communicated to smart tag 200 and/or to another processor via communication means CM.

Preferably, smart tag reader 42 receives information transmitted by smart tag 200 via an antenna or array of antenna 44, i.e. when smart tag 200 is within a space in which electromagnetic radiation from its antenna 220 is effective to be received by antenna 44 of the smart tag reader 42. In addition, and preferably, the smart tag reader 42 is a smart tag reader/writer 42 that also encodes and transmits information electromagnetically via its antenna 44 effective to be received by antenna 220 of smart tag 200 when in the detection region. Such smart tag readers and reader/writer 42 may be of any suitable type, including commercially available conventional reader/writers.

As described herein, the antenna 44 may be an all-orientation antenna array wherein the antenna are operated simultaneously and/or are either spatially separated or temporally separated by being activated sequentially in time to eliminate interference, and a single reader/writer unit 42 therefor may control and operate a plurality of antenna 44. It is noted that the use of an antenna array 44 that has the ability to detect smart tags 200 in its detection region with substantially 100% reading rate may be important to obtain the fill convenience advantage of the apparatus and/or method. Typically, substantially 100% reading rate means at least a reading rate of about 99%, and preferably a reading rate of about 99.5%, irrespective of the orientation of the smart tag within the detection region of the antenna array. It is noted that variations in the antenna and/or smart tags and/or reader/writer units, such as variations due to component, production, adjustment, tuning, matching and other tolerances, and variation over time and temperature, as well as any other sources of electromagnetic radiation incident on the antenna, may produce variation of those percentages.

Smart tag 200 includes an electronic device 210 and an antenna 220 by which information is provided and/or received. Electronic device 210 typically includes an electronic memory 214 in which information is stored and a processor 212. Processor 212 retrieves and codes information produced from memory 214 in a form suitable for communication via antenna 220 and/or electrical contacts 222. Preferably, processor 210 also codes and provides information received via antenna 220 and/or electrical contacts 222 and stores such information in memory 214.

The coding provided by processor 210 may include modulating and demodulating signals for radio frequency communication and/or converting information to suitable digital and/or analog signal format for communication via antenna 220, and may also include converting received information to a form, typical a digital format, for storage in memory 214. Processor 210 may also perform signal synchronization, authorization verification and/or encryption/decryption as may be deemed necessary and/or convenient.

Information including related information from smart tag 200 and from electronic gate 40, e.g., typically information that is a record of an object passing station 20 or plural stations 20. Such information may be produced from memory 32 of processor 30 or from memory 214 of smart tag 200, or both Optionally, electronic gate 20 may also include a display 50 and a data input means 52 coupled to processor 30 and to reader/writer 40 for communicating with a smart tag 200. Display 50 typically includes a visual display device such as a video or computer monitor, LCD display, cathode ray tube, dot-matrix display, touch screen display, or any other display providing information in a visual form that can be perceived (e.g., seen) by a person. Display 50 may also include an annunciator, loudspeaker, or other sound transducer for providing audible information that can be perceived (e.g., heard) by a person, such as an alarm or reminder or warning, e.g., via pre-recorded and/or synthesized speech Data input means 52 typically includes a keypad, keyboard, touch pad, light pen, or other device by which a person may enter information into electronic gate 20.

Display 50 and data input 52 may be used, for example, to monitor the objects passing or that have passed station 20 and/or for entering information to be stored in the smart tag of an object passing station 20, such as information indicating that the object has been manually inspected or otherwise received or should receive special handling or attention. Examples in the medical environment include, for example, inspection, quality control, searching for lost medication and/or devices, evaluation of operation and/or personnel, and the like.

Personnel may enter information requests and the like, i.e. requests for data items or specific records, via input means 52 which information is stored in a memory 32 associated with processor 30 or is transmitted to smart tag 200 via reader writer 40. In either case, information from smart tag 200 and information entered via input means 52 are related and stored in a memory, and typically provide a record of activity relating to station 20. The memory in which such information is stored may be memory 214 of smart tag 200, or may be memory 32 of gate 20, or both.

Also optionally, a printer to paper, or an electronic writing device that provides the information on other tangible media, such as floppy disks, CDs and other electronic media, may be associated with a particular station 20 or with a check-in or check-out station, either on a temporary or permanent basis. Such printer may be remote from a particular station 20 with information communicated thereto by conventional communication means including but not limited to wire, cable, optical fiber, local area network (LAN), wide area network (WAN), radio transmission, optical transmission or other suitable means, or any combination thereof, with or without one or more communication hubs.

Alternatively, display 50 may be a touch screen display 50 that provides an easy to use and convenient combined display 50 and input means 52 through which information may be provided and information and requests may be received. Input means 52, which may be optional in this embodiment, such as a standard computer keyboard, provides a input means through which information may be entered into processor 30.

Smart tags 200 are typically utilized for tagging and electronically identifying articles by reading information stored in the electronic memory of the smart tag using contact-less radio-frequency (RF) transmissions. Available smart tags operate at RF frequencies between hundreds of kilo-Hertz (KHz) and several giga-Hertz (GHz). Typical frequencies for RF smart tags and smart cards (functionally the same but different in form) include 125 KHz, 13.56 MHZ, 915 MHZ and 2.45 GHz. For medication and medical devices and implements, a smart tag of about 0.5 inch by 0.6 inch (about 1.2 cm by 1.5 cm) operating at 13.56 MHZ is typically preferred.

For the present smart tagging system and method, an electronic integrated circuit in the form of a semiconductor chip is connected to an antenna ANT on a substrate to serve as a tag. The semiconductor chip typically includes a processor and an electronic memory for storing information. Information stored in a smart tag can be read by a suitable smart tag reader and can be read and written to by a suitable reader/writer. The reader or reader/writer and the tag antenna are tuned suitably so that RF energy (electromagnetic fields and electrical signals) can stimulate the tag to emit a signal representative of the information (electronic codes or data) stored in the tag memory. Such contact-less RF tags eliminate the need for an electrical contact or a line-of-sight path for communication with the smart tag.

Suitable smart card/smart tag semiconductor chips include the I-CODE chip and the MIFARE chip, both available from Philips Semiconductors located in Eindhoven, The Netherlands, and the types SLE4442 or SLE4428 memory ICs available from Siemens of Germany. Also suitable are the "Tag-it" devices available from Texas Instruments of Dallas, Tex., the "Pico-Tag" devices available from Inside Technology of France, and devices available from Microchips of Phoenix, Ariz. Each smart tag/semiconductor chip must have sufficient memory for storing all of the information desired to be stored therein. Typically about 100-500 bytes is sufficient, one kilobyte or 1000 characters is preferred, and 2000 bytes or characters is better.

Suitable smart tags include those, such as an I-code chip, that conform to the ISO15693 format protocol for wireless RF identification tags, as is available from several commercial sources. Smart tags may also include an overwrite protection feature whereby information stored therein may be protected from being overwritten or changed, thereby to provide a measure of security.

Suitable smart tag reader/writers include those available from Avante International Technology, Inc. located in Princeton Junction, N.J., the Fast-Track system available from Escort Memory Systems located in Calif., the Interrogator Control Module available from Samsys Technologies, Inc. located in Calif., and the Memor 2000 RFID available from Minec company located in Taby, Sweden, as well as readers/writers available from Intermec Technologies Corporation located in Everett, Wash., Fargo Electronics, Inc. located in Eden Prairie, Minn., or from Atlantek, Inc. located in Wakefield, R.I.

Suitable processors (both local processor LC and central processor 200) include any modern personal computer (PC), such as those having a Pentium®, Celeron®, or similar processor, running a Windows, Unix or other PC operating system. Where a LAN or WAN network is employed, standard PC networking hardware and software may be included in the PCs. Desirably, the processors, as well as the smart tag control units readers/writers, will have redundant memory and information storage, such as by one or more of non-volatile memory, a hard disk drive, a floppy disk drive, a CD-write drive and the like.

Applications programs suitable for recording and manipulating the information include relational database software such as the Windows-NT-based Microsoft ACCESS database as well as ORACLE, SYBASE and INFORMIX database software, and software languages such as Visual Basic, Java, or other language compliant with American National Standards Institute (ANSI) Standard 256. Each database record will typically include fields some or all of the following information: The article identification and/or Ser. No. and/or quantity, station and/or operation identification, entry and exit time data (arriving and leaving), date, bill of material data, actual/planned material usage, keypad/keyboard entered data, component/part/material smart tag information, operator/employee/individual smart tag information, quality control and inspection data, transport provider, and the like. Thus, the database maintains an inventory of the articles, their quantities and locations and may be utilized to categorize the data contained in the database records for tracking any article or any type or group of articles, and/or any station so also provide status and inventory by station, operator or any other desired category of the stored records. Typically, the database software interfaces with other standard software, such as the standard MRPII software available from the Great Plains division of Microsoft Corporation of Redmond, Wash.

Desirably, processed information and/or transactional information should be available in human readable form, such as by display on a computer monitor or by print out by a computer printer, both of which may be conventional. Where certain information recorded and/or processed is representative of parameters or conditions that may pose a hazard to personnel or property, or are critical to an operation or process, or indicate a failure of some test or condition, it is desirable to include an alarm, such as a loudspeaker, flashing light, buzzer, speech synthesizer, or the like, that is activated automatically by an out-of-limit or marginal condition.

Figure 4A:
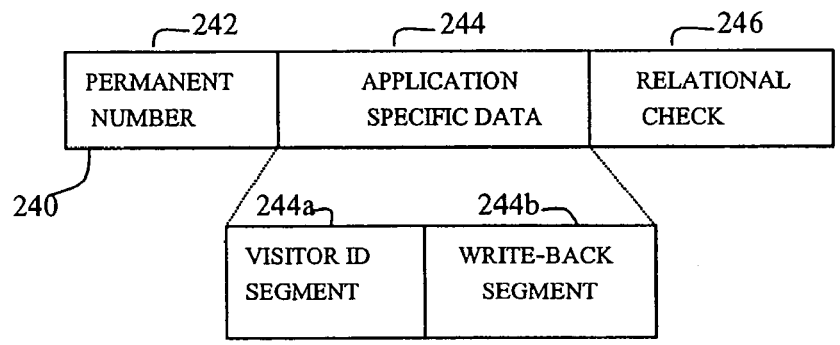
FIGS. 4A, 4B and 4C are schematic representations of memory allocations and relational database arrangements suitable for use with the apparatus and method described herein.

FIG. 4A is a schematic representation of a memory allocation 240 suitable for a smart card 200 for use with the apparatus and/or method. Sections 242, 244, 246 of memory EM of smart tag ST are allocated or segmented for the storage of particular information. Typically, an EEPROM memory is utilized.

Manufacturers of the electronic devices or chips utilized in smart tags typically segment the memory thereof into two segments: a first segment 242 into which the manufacturer burns in (i.e. permanently stores in a way that the information cannot thereafter be changed) a unique identifier of the electronic device or chip. Such permanent number 242 may be tens or hundreds of bits in length, as is appropriate for providing a unique identifier. The remainder of the memory capacity 244, 246 is left available for the storing of data therein in use, which data may be modified, written over or otherwise changed in the use of the electronic device.

Smart tags 200 are typically utilized for tagging and electronically identifying objects by reading information stored in the electronic memory of the smart tag using contact-less radio-frequency (RF) transmissions. For the present smart tagging system and method, an electronic integrated circuit in the form of a semiconductor chip is connected to an antenna on a substrate to serve as a tag. The semiconductor chip typically includes a processor and an electronic memory for storing information. Information stored in a smart tag can be read by a suitable smart tag reader and can be read and written to by a suitable reader/writer. The reader or reader/writer and the tag antenna are tuned suitably so that RF energy (electromagnetic fields and electrical signals) can stimulate the tag to emit a signal representative of the information (electronic codes or data) stored in the tag memory. Such contact-less RF tags eliminate the need for an electrical contact or a line-of-sight path for communication with the smart tag.

While it is satisfactory to utilize only the stored permanent number identifier 242 to identify the smart tag containing the electronic device, it is preferred that the permanent number 242 be stored in a relational database in a processor and be linked to other identifying or use information for use in identifying the object or article to which the smart tag is attached or with which it is associated. Such processor is in communication with the smart tag readers that read information from memory 240 of the smart tags.

One potential problem associated with such smart tags occurs where the information desire to be stored therein is simply coded and written into the writeable memory 244, 246. In that case, any change to the information stored therein is undetectable. Typical sources of erroneous or corrupted or erased data include electromagnetic interference, whether accidental or intentional, as well as any intentional or unintentional attempt to modify the stored information, whether authorized or unauthorized, such as by a thief or counterfeiter. Having other than the correct data stored in the memory of the smart tag can lead to misdirection, loss or damage to property and/or injury to person, none of which is desirable or acceptable.

To reduce the likelihood of undetected erroneous stored information, the remaining memory 244, 246 available to the smart tag user is further segmented into two segments. The first segment 244, which is typically of greater memory capacity, is allocated for the storage of application specific data, such as the article identification, manufacturer, batch or lot identification and other information, 244a, and for information 244b that is written back to the smart tag memory by the smart tag reader/writer at the various stations, such as station identification, operation performed, date and time, and the like. The second and smaller memory segment 246 is allocated for storing a relational check number or code that is a calculated or coded value representative of at least the value of the stored application specific data, and preferably representative of the value of both the permanent number and the application specific data. Herein, the relational check number or code is usually referred to simply as the relational check number to include numbers and/or codes.

Where the smart tag includes processing capability, the processor can be programmed to calculate the relational check number upon each time data is written to its memory, preferably upon command to do so. Alternatively or additionally, each reader/writer or an associated processor or central processor can calculate the relational check number. Because the electronic device utilized in a smart tag has substantial memory capacity, the relational check number can include many bits and so can be constructed to permit error correction as well as error detection.

The foregoing arrangement permits detection of errors and/or changes to the application specific data at any time by reading the card and recalculating the relational check number which is then compared to the relational check number read from the smart tag. If the read and calculated relational check numbers match, then there is a high degree of certainty that the application specific data has not been changed and does not include errors.

It is noted that while the permanent number, the application specific data and the relational check number or code are referred to as "numbers," each may include numerical, alphabetic, alpha-numeric and other characters and symbols, conventional or arbitrary, as may be desired. The relational check number or code is representative of the information stored in the memory in accordance with a predetermined formula or algorithm or other scheme, either on a character by character basis or on the basis of one or more combinations of the characters or values stored in the memory. Suitable formula and algorithms include, for example, parity checks or other parity representations, sum checks, field relationship checks or any other predetermined relationship between the stored permanent number and application specific data values and the relational check number.

Thus, any change to the stored information, including a change that changes the stored value of the relational check number or code, will be detectable and an indication that the stored data contains one or more errors or changes. Typically, the particular formula or algorithm that generates the relational check number is not known to third parties and is not derivable from the data stored in the smart tag memory, and so the relational check number provides a degree of security for the information stored in the smart tags.

The formula or other algorithm or other encoder for generating the relational check code or number may be provided in protected firmware, in software or in a combination of firmware and software, to provide a higher level of security against deciphering or unauthorized coding. For additional security, each encoder may also include a unique identifier that must be paired with coding software having the same unique identifier for enabling proper functioning. The unique encoder identifier may also be included in or as part of the application specific data.

Figure 4B:
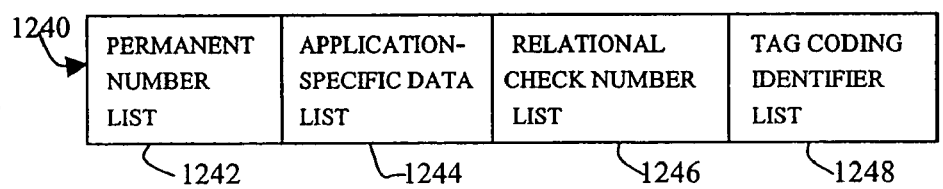
Figure 4C:
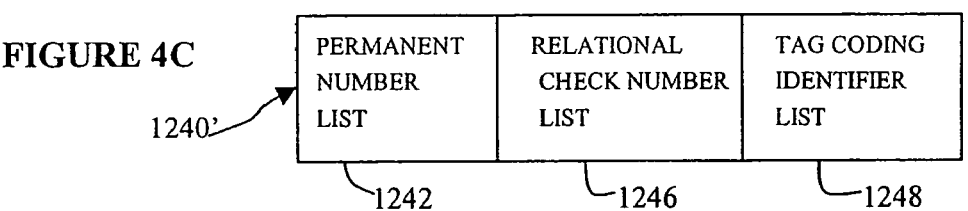

FIGS. 4B and 4C are schematic representations of memory allocations of a relational database of a processor suitable for use with the apparatus and/or method. Database 1240 represents an aggregation of records stored in relational database computer software running on a processor. Compiling records of data written to smart tags in a relational database is particularly advantageous where the data is written to the smart tag and where it is important to be able to retrieve such data should the smart tag be misplaced, lost or stolen, or if the information stored therein is changed or corrupted or lost for any reason.

In a complete database, database 1240 illustrated by FIG. 4A stores a record each time data is written to any smart tag used with the tracking system Database 1240 includes, for example, a number of data fields comprising a list 1242 of the permanent numbers of the smart tags, a list 1244 of the application specific data of each writing of application specific data to each smart tag, a list 1246 of the relational check number written to each smart tag with each writing of application specific data thereto, and a list 1248 of tag coding identifiers such as the date, time, reader/writer identification for each writing of application specific data to each smart tag. Lists 1242, 1244, 1246, 1248 are comprised of aggregations of records corresponding to each writing of information to each smart tag, and may be provided from one or both of the smart tag and the reader/writer utilized for each writing of information.

In a simplified database, database 1240' includes, for example, lists 1242, 1246 and 1248. This database arrangement may be advantageous where the database is stored in a local processor and/or a smart tag reader/writer where available memory capacity may be more limited than in another processor. In either a complete or simplified database, information relating to each writing of information to each smart tag is communicated to a processor in real time or delayed, and may be periodic or aperiodic. Information may be communicated by any of the means described as well as by manual communication, e.g., by transporting the smart tag reader/writer and/or local processor and/or computer media containing the information stored in such smart tag reader/writer and/or local processor to another processor.

Suitable relational database software include ACCESS and SQL Server database software which runs on conventional PC processors with standard operating systems, such as Windows-NT, both available from Microsoft Corporation of Redmond, Wash., as well as the ORACLE, SYBASE and INFORMIX database software. Preferably the database software is "Internet-ready" in that it includes features facilitating connection to and communication of information via the Internet.

Each database record will typically include fields for some or all of the following application specific data or information in addition to the permanent number:

Object information including but not limited to the identification of the object, its manufacturer, its dispenser and/or shipper, its patient and/or recipient, the identification of the mode of, time of, dosage of and/or frequency of administration, conditions of use, refill and expiration information, and/or other identifying information, and the like.

Station information including but not limited to station identification, operator/personnel identification, entry and exit time data (arriving and leaving), date, expiration date, keypad/keyboard entered data, smart tag information, quality control/inspection information, and the like.

Relational check number representative of any or all of the foregoing application specific data and/or the permanent number of the smart tag.

Where the information written to each smart tag is all communicated to and stored in a central database and where all subsequent action to be taken will be taken based upon the information stored in the central database, then the use of a relational check number to verify the information stored in the smart tag and/or detect errors in and changes thereto is of much less importance.

In any case, the central database can be utilized to provide particular information, general information, status information, statistical information, and other information on an on-line basis that is at least as current as the entry of record information into the database. Where every writing of information to a smart tag is also replicated in a record stored in the relational database, the relational database contains and can provide a detailed history of the utilization of the smart tag, e.g., the path of the object's movement and the date and time of its passing each station as well as information entered at each such station.

Figure 5A:
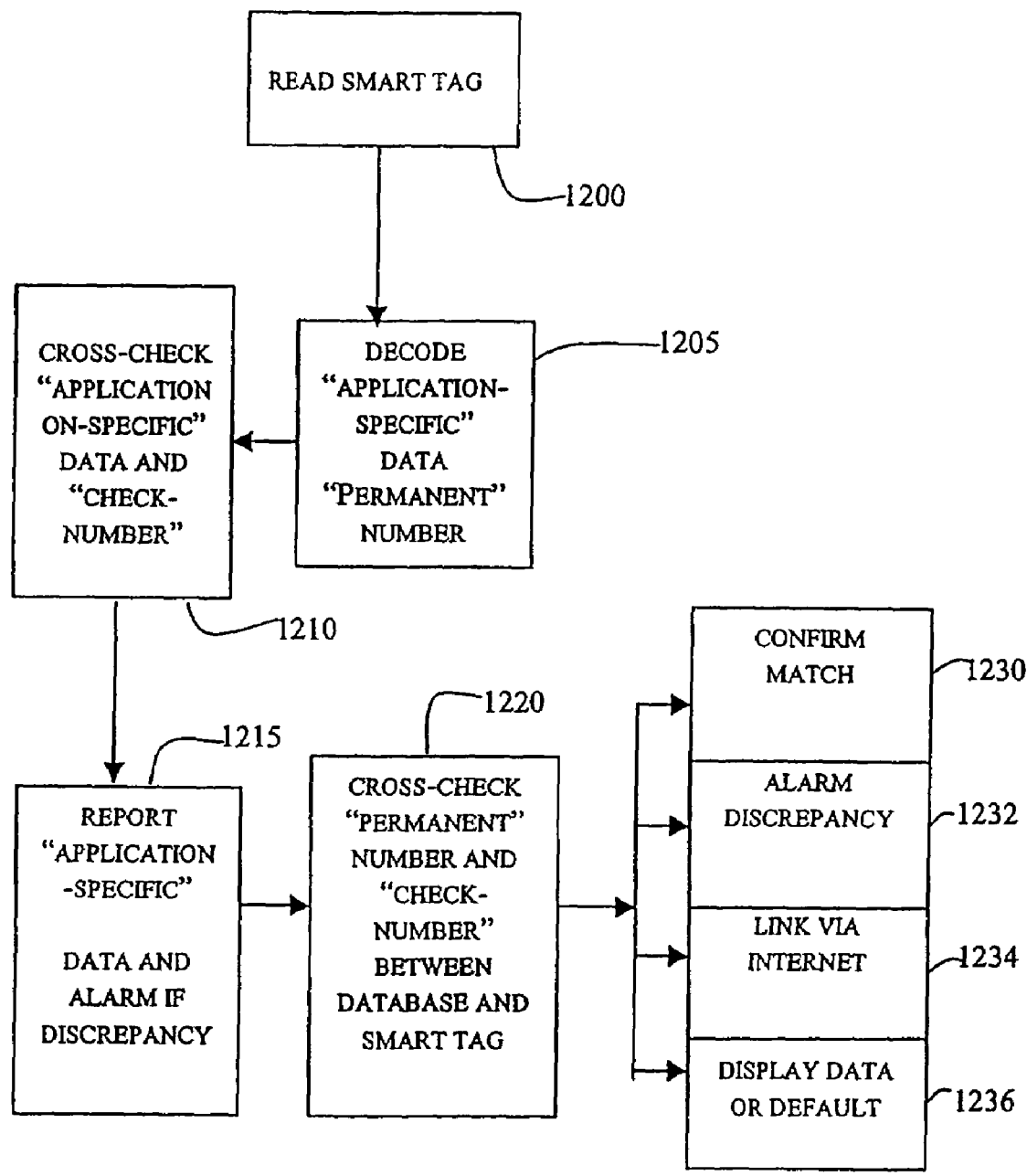
FIGS. 5A and 5B are flow chart schematic diagrams illustrating examples of a utilization of the memory allocations and relational database arrangements of FIGS. 4A-4C.

FIG. 5A is a flow chart schematic diagram of an example of a utilization of the memory allocations 242, 244, 246, and of memory allocations and relational database structures 1242, 1244, 1246, 1248 of FIGS. 4A-4C. Information from the smart tag is read 1200, such information including, for example, a permanent number related to the particular smart tag, application specific data relating to the article and stations, and a check number representative of at least the application specific data and preferably the application specific data and the permanent number. Application specific data read from the smart tag is decoded 1205 and the permanent number read from the smart tag is stored.

A cross check 1210 is made between the application specific data and the permanent number read from the smart tag. Cross check 1210 includes calculating from the application specific data and the permanent number the value of the check number and comparing that calculated value to the value of the check number read from the smart tag. If the two check numbers correlate, then there is a high degree of confidence that the application specific data does not contain errors and has not been altered. It is noted that cross check 1210 is performed at least initially using only the information read from the smart tag and so does not necessarily require a central processor or database. If there is a non-correlation or other discrepancy, such non-correlation or discrepancy produces an alarm 1215 and further correlation steps may be taken.

Results of the reading of smart tags and of the correlation of the check numbers thereof are reported 1215 in any convenient form. Such reporting may be by aggregation of records in a database for current or delayed review, by displaying the results or summaries of results or statistics related to results on a human-perceivable display, or by initiating an alarm or alert 1215 of lack of correlation of check numbers. Such alarm may take the form of a print out, a paper document, a visual display, a warning screen, an audible signal, synthesized speech, a signal to a control or monitoring station or to a pager or cell phone, or any other convenient form of alarm, alert or signal.

A further cross check 1220 may be made to check at least the permanent number and relational check number stored in the database to the permanent number and relational check number read from the smart tag. Because the permanent number of a smart tag cannot be changed, cross check 1220 includes comparing the relational check number read from a particular smart tag having a given permanent number with the relational check number stored in the relational database for the most-recent record corresponding to that given permanent number. Correspondence or lack of correspondence of the respective relational check numbers from cross check 1220 is utilized to confirm such correspondence or lack thereof by human-perceivable display or alarm or alert, as described above.

In particular, correspondence in cross check 1220 initiates confirming a match 1230, e.g., by any human-perceivable display, report or alarm, as described above. Lack of correspondence in cross check 1220 is a discrepancy that initiates giving an alarm 1232, e.g., by any human-perceivable display, report or alarm, as described above.

Initiating a human-perceivable display or alarm, or communicating information to or from another location can include linking 1234 the processor performing any of cross checks 1210 and 1230 and/or producing a report or alarm 1215, 1230, 1232, to a remote processor, display or alarm via the Internet. Such linking via the Internet 1232 may include accessing a remote relational database, which may be an open database to which information can be added, deleted or changed or which may be a closed database not allowing information to be added, deleted or changed via the Internet link. Access may be controlled by access codes, passwords and the like as desired, and information communicated via the Internet may be encrypted, to provide the desired degree of security.

Further, correlation or lack of correlation or any other difference between the information read from a smart tag and the related information stored in the relational database initiates displaying 1236 data from any one or more of the smart tag and a local or central relational database, or if such data is limited or missing, displaying 1236 a default indication, e.g., whatever information is stored in the database. Displaying 1236 may include displaying information from the smart tag and the relational database or may be limited, e.g., to displaying the differences and/or discrepancies of that information, and may be immediate or delayed. Displaying 1236 may be for each cross check 1210, 1220, or may be for any number of cross checks 1210, 1220.

The display of the result or status of any step and/or of the information to which attention is to be drawn may be included in a display of information, e.g., such as by highlighting or coloring the portion of the displayed information to which attention is to be drawn, or by separately displaying the information to which attention is to be drawn. Where information desirable to be displayed is available in the relational database, such information is retrieved and displayed automatically, either locally, remotely or via the Internet, as appropriate. If such information is not so available, a warning or instruction to an operator is provided to instruct the operator to either retrieve the information or to segregate or mark the affected smart tag for special treatment or handling, e.g., such as alerting an attendant or operator at final or check out station when an article associated with that smart tag arrives.

It is noted that the foregoing arrangements and method also can enable the detection of changing or tampering with the information stored in the smart card for the unlikely case where the changing or tampering is done with knowledge of the calculation of the relational check number. In such case, the relational check number is correctly related to the application specific data and/or the permanent number and so the simple cross checking 1210 will not detect the changing or tampering. Because the information written to each smart tag is also stored in the relational database correlated to the smart tag unchangeable permanent number, comparison of the changed or tampered-with information read from a smart card is detectable by cross checking 1220 that read information against the information stored in the relational database.

Where desired, the relational database may be accessed and made available by any convenient means, e.g., by providing same on floppy disk or CD-ROM, optical CD and the like that is easily sent by mail, express and the like, or by making same available via communication means such as wire, cable, optical fiber, LAN, WAN, optical or radio frequency transmission, the Internet and the like.

Figure 5B:
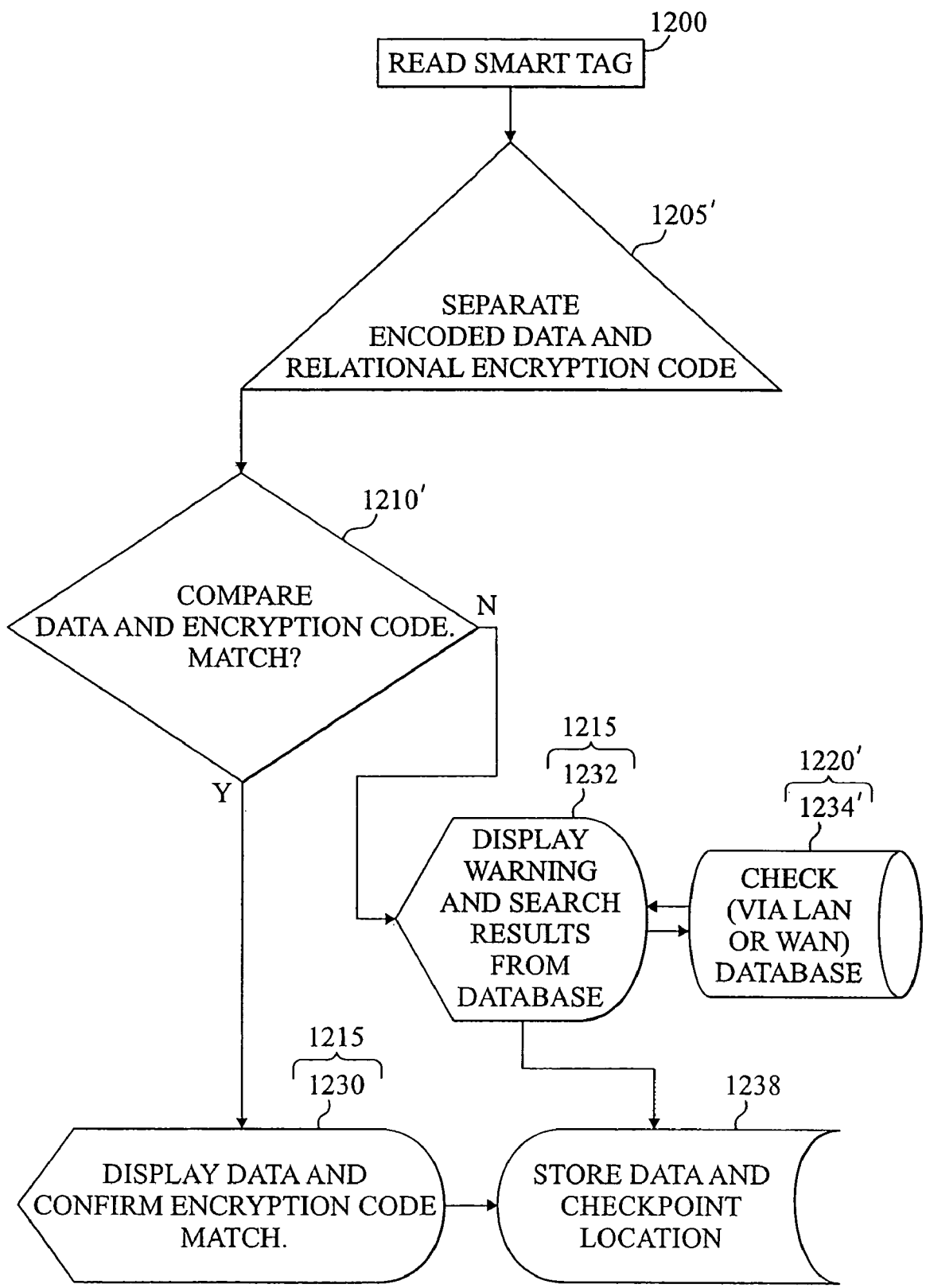

FIG. 5B is a flow chart schematic diagram of another example of a utilization of the memory allocations 242, 244, 246, and of memory allocations and relational database structures 1242, 1244, 1246, 1248 of FIGS. 4A-4C. It is noted that the steps of FIG. 5B include steps as described above in relation to FIG. 5A, but arranged for a more direct illustration of certain steps. Information from the smart tag is read 1200, such information including, for example, the permanent number related to the particular smart tag, application specific data, and a relational check number (also referred to as a "relational encryption code") representative of at least the application specific data and preferably the application specific data and the permanent number.

The encoded application specific data and relational check number read from the smart tag are decoded and separated 1205' and are compared 1210' to determine whether the relational encryption or check code or number read from the smart tag corresponds to or matches the relational encryption or check code or number recalculated by the processor from the application specific data and the permanent number read from the smart tag. I.e. match 1210' is a cross check that includes calculating from the application specific data and the permanent number the value of the relational check number and comparing that calculated value to the value of the check number read from the smart tag.

If the two check numbers correlate (i.e. match, path "Y"), then there is a high degree of confidence that the application specific data does not contain errors and has not been altered, and the application specific data is displayed 1215/1230 along with confirmation that the relational check number correlates.

If there is a non-correlation (i.e. non-match, path "N") or other discrepancy, such non-correlation or discrepancy produces the display of a warning or alarm 1215/1232 and initiates further correlation steps. Such further steps include retrieving 1220'/1234' from a relational database records stored therein corresponding the particular smart tag related, for example, by its permanent number, and displaying or posting 1215/1232 such retrieved stored records. Access to the relational database, if not direct in the processor, is by communication 1220'/1234' with a processor via communication means, typically a LAN or WAN, or via the Internet.

Whether there is correlation or non-correlation of the relational check number, a record is stored 1238 in the relational database including the information read from the smart tag in step 1200, whether or not the read data correlated or not in step 1210', and the identity of the station or check point at which such data was read.

Figure 6:
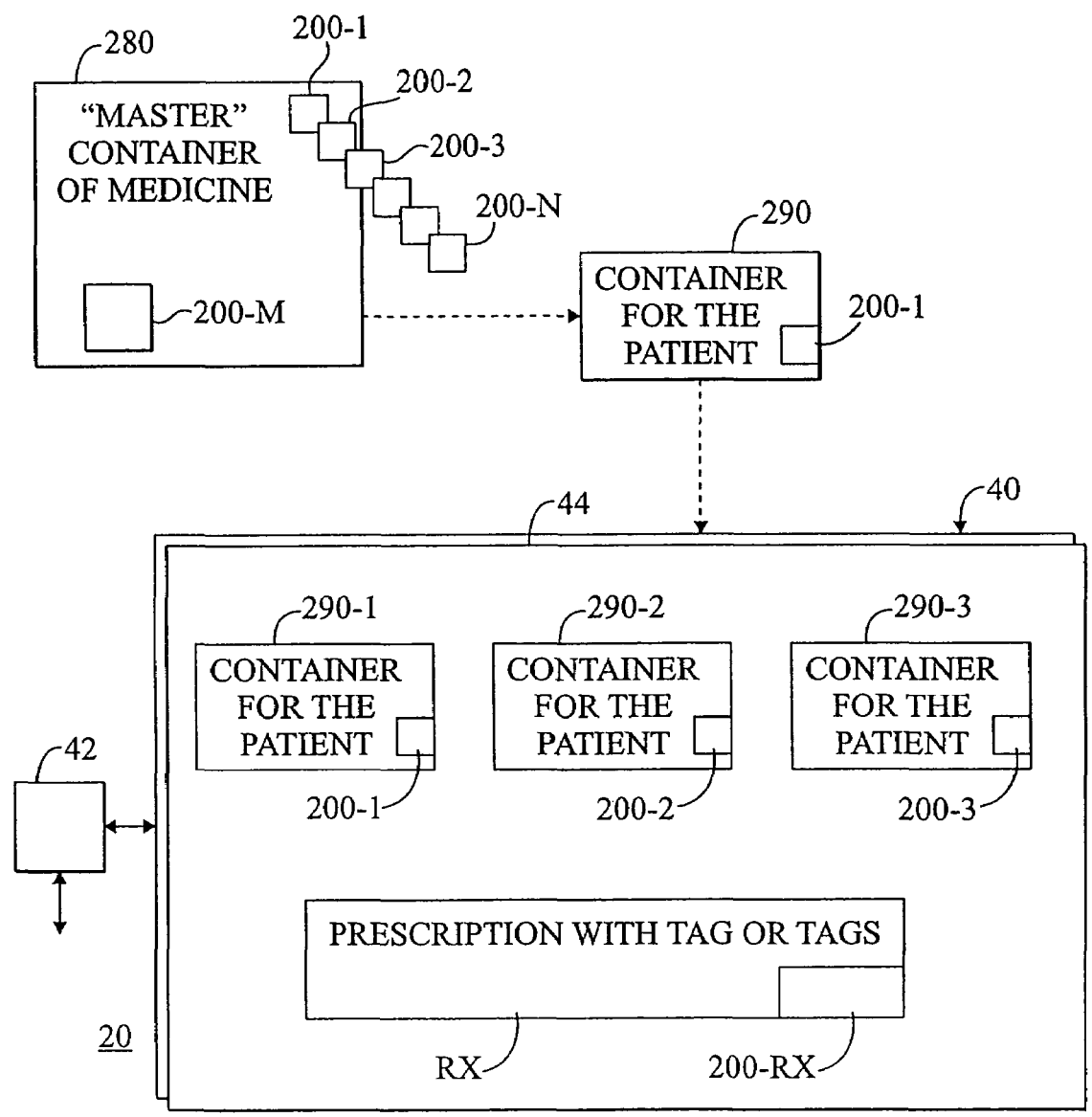
FIG. 6 is a schematic diagram illustrating an arrangement employing smart tags in an environment for processing medicine.

FIG. 6 is a schematic diagram illustrating an arrangement employing smart tags 200 in an environment for processing medicine or medication, medical devices and/or medical implements. Herein, medication is used and is deemed to include medication and medicine in whatever form, as well as medical implements, devices and other equipment of any sort, and is representative of any other thing that is to be dispensed or issued in a controlled manner.

Medication is provided, for example, in bulk or quantity in a container referred to as a "master" container 280 that contains plural doses of the medication. Medication may be received in container 280 or be placed into container 280 or be in inventory in container 280, e.g., by a manufacturer, distributor, pharmacy or physician. Doses or units may be "loose" as in the case of a large number of scalpels, syringes, pills or tablets in a bottle, jar, cannister or other container, or may be separately wrapped as in the case of a number of scalpels, syringes or bottles of pills in a box or carton. A master smart tag associated with carton 280 contains information identifying the medication, quantity, dosage, expiration, lot and date, NDC number, and the like.

In addition, plural smart tags 200-1, 200-2, . . . 200-N are associated with each package or dose. Smart tags 200-1, 200-2, . . . 200-N may be included in master container 280 or may be encoded and issued by the holder of container 280, e.g., by a manufacturer, distributor, pharmacy or physician. As doses/units or dispensing of the medication is ordered, the medication is placed in a dose or unit container 290, e.g., a smaller container for individual use, and one of the smart tags 200-1, 200-2, . . . 200-N is associated with that smaller container 290. Smart tag 200 is at this time encoded to have stored therein patient and treatment information in addition to the medication information, as described above. Each smart tag 200 is typically firmly attached or affixed to a respective container 290, e.g., adhesively.

In dispensing or issuing the medication, each individual dose/unit container 290-1-290-3 is placed into or passed through a smart tag tracking station 20. In particular, containers 290-1-290-3 with respective object smart tags 200-1-200-3 attached are placed within the detection region of electronic gate 40 including smart tag reader/writer 42 and antenna array 44 as described. Also placed into or passed through gate 100 is the particular prescription or order Rx having check smart tag 200-Rx therewith.

Reader 42 reads the information stored in smart tags 200-1-200-3 and 200-Rx and cross checks such information to determine whether the medication dispensed as read from smart tags 200-1-200-3 matches the medication ordered as read from smart tag 200-Rx. If they match, then a confirmation is displayed or provided. It is noted that a match indicates that the order has been filled completely as well as accurately. If they do not match, an alert or alarm is provided, all as described above. The result of such cross check may be stored in a relational data base, may be cross checked against other information stored in a relational database, or may be related to patient, allergy, treatment norms or other information stored in a relational database, whether the information is in one database or in plural linked databases.

Herein, such checks and/or verification and/or matching typically include verifying that the information stored on the smart tag has not been altered, tampered with or otherwise changed. Such verification typically utilizes the relational check number and/or the smart tag overwrite protection feature, where such are included in the information stored on the smart tag, thereby to provide a measure of security.

Figure 7:
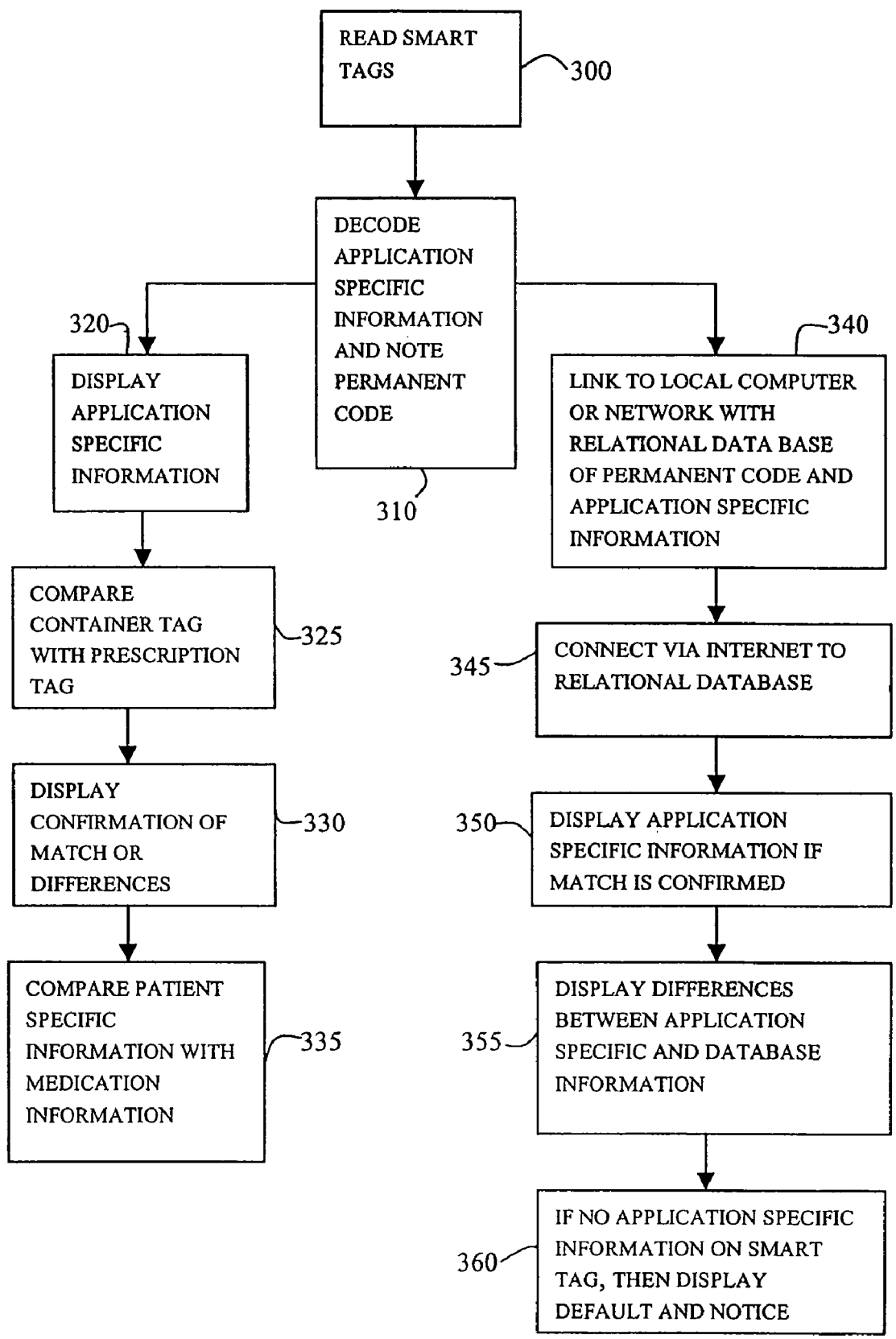
FIGS. 7 and 8 are flow chart schematic diagrams illustrating examples of tracking systems and methods useful in an environment for processing medicine.

FIG. 7 is a flow chart schematic diagram illustrating an example of a tracking system and method in an environment for processing medicine. The container (object) and prescription (check) smart tags are read 300 by a smart tag reader, e.g., as in a SMART-TRAKKER™ tracking station from Avante International Technology. The application specific information read is decoded 310 and the permanent number or code identifying the smart tag is read and noted or recorded 310, such data now being available for comparison, cross checking and/or other use.

Application specific information from each container smart tag is displayed 320, e.g., displayed separately (individually) if plural smart tags are present in the smart tag reader, as in a list or manifest. If the prescription smart tag is present, then the application specific information from the prescription tag is also displayed and is compared 325 against that from the container smart tags. Also displayed 330 is a confirmation that the application specific information from the container and prescription smart tags matches or an alert or alarm that such information does not match. In addition, patient specific information read from either smart tag is compared 335 with patient information and/or medical information (such as allergy, drug interaction or overdose information) stored in a relational database.

Further, the application specific information and/or permanent number read and decoded/recorded 310 from the smart tags may be linked 340 with a relational database (e.g., by local computer or network) to be stored therein and/or compared with similar information previously stored therein. If such information is not available in a local computer or via a network link, connection 345 may be made via the Internet to a remote relational database and the information is stored and/or compared as described, wherein access to such relational database is controlled by password, access code, encryption or other security means. In use, information in the database is typically updated and so a complete history of a patient's medication and treatments becomes accumulated therein.

If a match of the information read 310, 320 and/or the information obtained 340, 345 from the relational database is confirmed, that information and a confirmation of a match is displayed 350. If the information does not match in any respect, the differences between the information read 310, 320 from the smart tags, the information obtained 340, 345 from either a local or remote relational database is displayed 355 and preferably is highlighted or otherwise made apparent to alert or give alarm to appropriate personnel. If no application specific information is found on either or both smart tags, then a notice thereof is displayed 360 and any information in the relational database related by smart tag permanent number may also be displayed 360.

Figure 8:
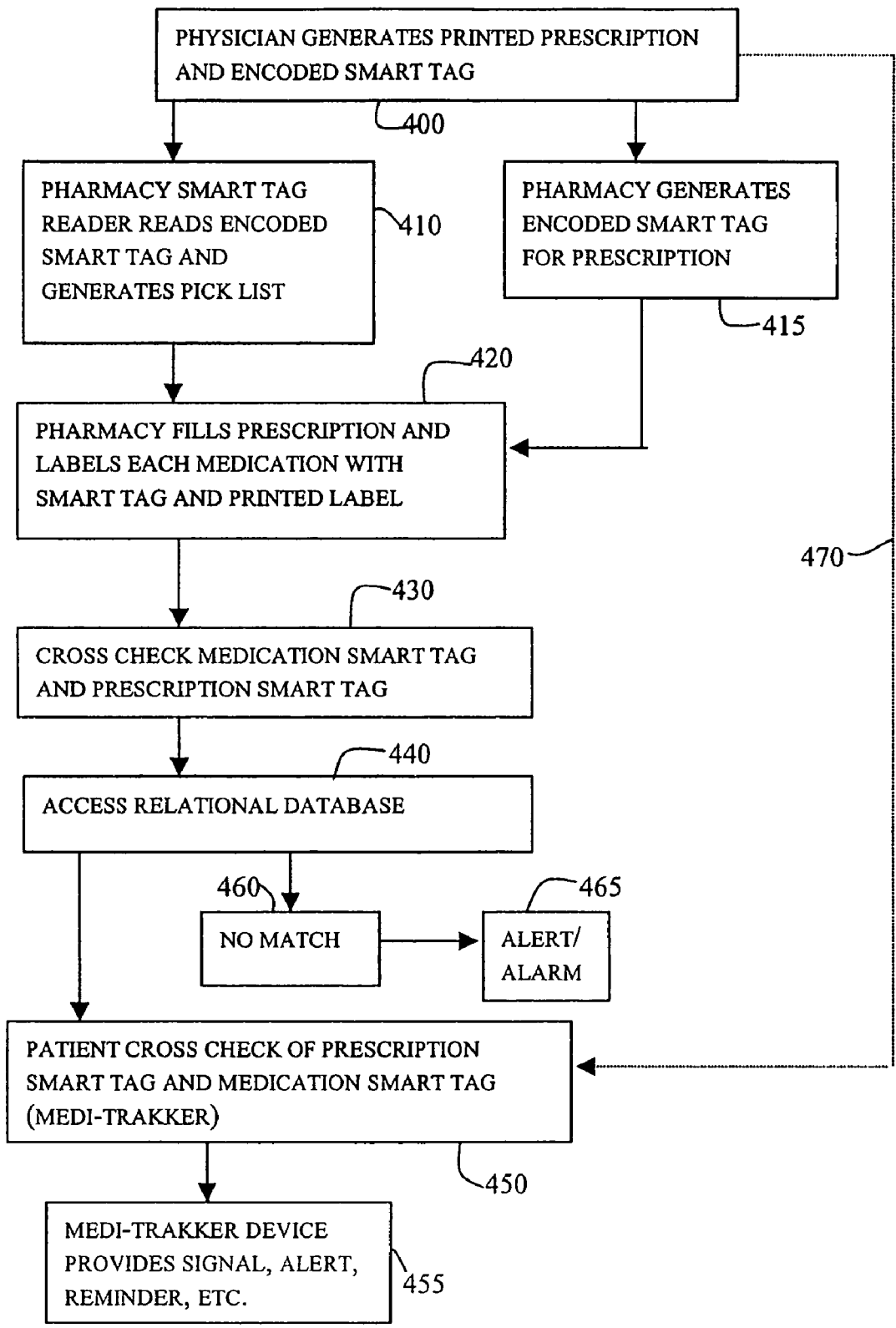

FIG. 8 is a flow chart schematic diagram illustrating another example of a tracking system and method in an environment for processing medicine. A physician generates 400 a prescription or order embodied in a printed prescription or order with an encoded smart tag attached, wherein the smart tag is encoded 400 with the prescription information (e.g., medication, dosage, frequency, number of refills, etc.), patient information (e.g., name, address, etc.), and physician information (e.g., name, address, license number, etc.). In addition to the foregoing information essential for the prescription to be filled, other information such as patient allergies, age, insurance, illness or disease or condition, diagnostic information, and the like, may also be encoded.

In filing the prescription, a smart tag reader at the pharmacy or other dispenser reads 410 the prescription smart tag and produces or generates 410 a pick list from which a pharmacist or other dispensing agent can fill the prescription. The pharmacy fills the prescription and labels 420 each item dispensed with a smart tag in which is stored the medication and prescription information. The pharmacy also applies a conventional human-readable printed label which may also include bar-coded information. If the physician does not generate a smart tagged prescription, then the pharmacy encodes 415 one or more prescription smart tags as it generates the pick list from which is fills 420 the order.

When the prescription is filled, the medication smart tag and prescription smart tag are read and cross checked 430 for completeness and accuracy, e.g., being placed in a tracking station as described herein, for example, a SMART-TRAKKER™ station or a MEDI-TRAKKER™ station or an MD-HELPER™ station available from Avante International Technology. If an error is found (no match) 460, an alert or alarm is provided 465, e.g., by recorded and/or synthesized speech. Such reader maybe linked to access 440 a relational database for comparing the information read from the smart tags with a medical database for verifying and/or identifying allergy, drug interaction, diagnostic or other information. Any potential problems or concerns generate a warning or alert 465 to the pharmacist or patient, e.g., by recorded and/or synthesized speech, so that consultation with the physician may be had.

Where the tracking station includes a smart tag reader/writer, as is preferred, information may be written to the smart tags as well as read therefrom, e.g., as part of access 440. For example, when a prescription is filled, the MEDI-TRAKKER™ or MD-HELPER™ station can read the number of refills permitted or remaining from the prescription smart tag, subtract one therefrom and write (as part of access 440) the then remaining number of refills to the memory of the prescription smart tag.

The present apparatus and/or method also provides an opportunity for the patient to confirm the correctness of his prescriptions and/or receive assistance in the proper administration thereof when or after the medication is dispensed. To that end, a patient may have a personal smart tag reading device, sometimes referred to as a MEDI-TRAKKER™ or MD-HELPER™ device by Avante International Technology, that at least reads the medication and/or prescription smart tags and may compare or cross check 450 the information read therefrom to provide an indication of whether the smart tags match or do not match This permits the patient to independently confirm that the medication and prescription smart tags indicate that the proper medication was dispensed. Such device is particularly useful in the case where the physician issues 400 a prescription with an encoded smart tag affixed, but the pharmacy does not use 470 the smart tag to verify the medication dispensed even though a medication smart tag is associated with the medication.

The MEDI-TRAKKER™ or MD-HELPER™ device for personal or home use may include all of the apparatus of the SMART-TRAKKER™ tracking station described above, or may be a simplified device. For example, a simplified MEDI-TRAKKER™ or MD-HELPER™ device need only include a basic smart tag reader and a simple processor for comparing a limited portion of the application specific information read from medication and prescription smart tags, and so could be relatively inexpensive and affordable. The antenna associated therewith need not be one that has substantially 100% reading rate irrespective of smart tag orientation, but may be a simpler inexpensive antenna, e.g., as described below. Such MEDI-TRAKKER™ or MD-HELPER™ device can read the medication information from the smart tag of the medication container and reproduce at least the information therefrom, for example, as synthesized speech, and may also augment such information, so as to assist persons who are visually impaired.

A MEDI-TRAKKER™ or MD-HELPER™ device having additional features provides the patient with a display of the information read from the smart tags, and/or provides 455 a reminder (e.g., by visual and/or audible alarm and/or recorded and/or synthesized speech) of times to take medication. In such case, the MEDI-TRAKKER™ or MD-HELPER™ device may include an acknowledgment or confirmation button or other input device by which the patient can indicate to the MEDI-TRAKKER™ or MD-HELPER™ device the fact that the medication was taken and the time thereof, and/or the patient can simply place the medication container having a smart tag within the detection region of the antenna thereof.

A MEDI-TRAKKER™ or MD-HELPER™ device having further capability could, for example, either include or be coupled to a microprocessor, computer or other processor, e.g., a laptop computer, which includes a relational data base of patient information and/or medical information for providing 455 reminders, signals and alerts of times and dosages of medications to take, audible and/or spoken reminders to obtain refills or physician re-authorization, and/or possible allergic reactions, drug interactions, inappropriate treatments and the like (e.g., by visual and/or audible alarm and/or recorded and/or synthesized speech).

Figure 9:
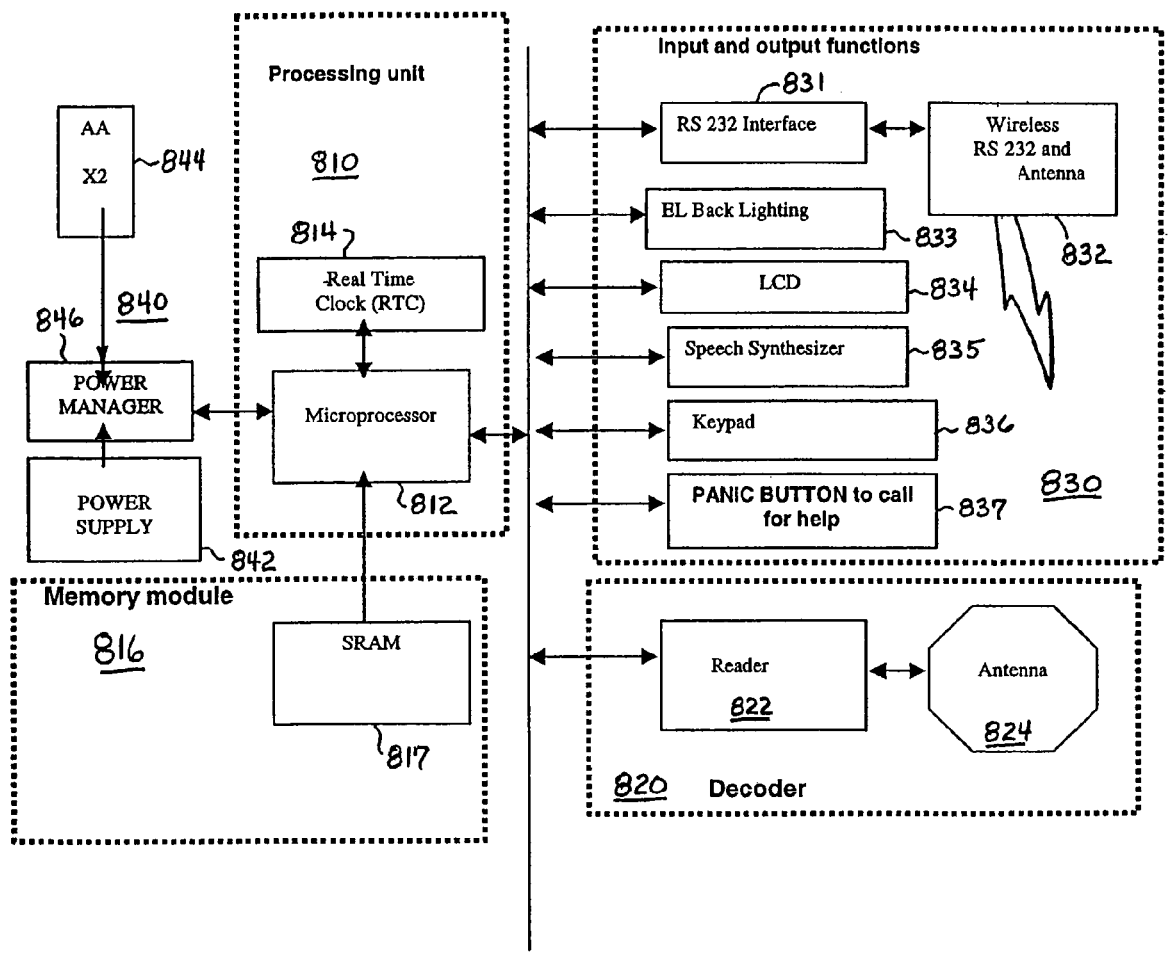
FIG. 9 is a schematic block diagram of an example embodiment of a medical tracker apparatus.
Figure 9:
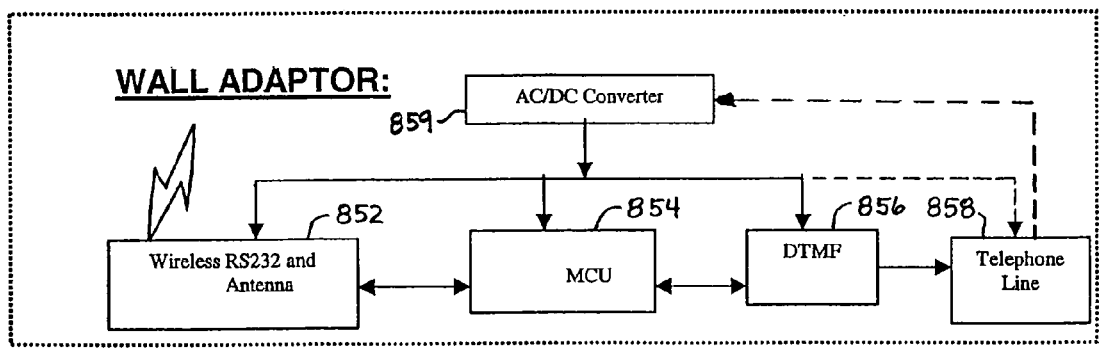

FIG. 9 is a schematic block diagram of an example embodiment of a medical tracker apparatus 800, such as apparatus of the MEDI-TRAKKER™ or MD-HELPER™ device type. Apparatus 800 includes a processing unit 810, a smart tag reader/decoder 820, a memory 816, an input/output (I/O) 830 and a power supply 840. Processing unit 810 includes a microprocessor 812, such a type 8051F020 low-power processor available from Cygnal Integrated Products, Inc., located in Austin, Tex., and a real-time clock 814 for providing day, date and time information to processor 812.

Associated with and coupled to processor 812 is a memory 816, including, for example, a static random access memory (SRAM) 817, preferably of 32 kilobytes or larger capacity. Information stored in memory 816 includes, e.g., information read from smart tags associated with medications, medical devices and/or implements that have been placed within the detection region of an antenna 824 that is associated with apparatus 800 (described below), as well as additional information entered via keypad 836 and/or display 834 where display 834 is a touch-screen device. In addition, information pertaining to drug interactions, acceptable dosages and frequencies of administration, telephone numbers and other contact information for emergency contacts, and the like may also be stored therein. Static memory, i.e. memory that retains the information stored therein, is preferred so that information is not lost should power to apparatus 800 be interrupted, either accidentally or intentionally.

Apparatus 800 is provided electrical power by power source 840 which includes a power supply 842 typically providing DC power, e.g., at 6 volts and up to about 0.4 ampere, from the local power mains, e.g., a wall outlet. Apparatus 800 also includes a battery 844, e.g., four size AA battery cells, for providing power at tines when power is unavailable from power supply 842, e.g., during times of power outage due to storm, blackouts, and/or equipment problems, or when apparatus 800 is unplugged from a wall outlet in being moved to another location. Battery 844 may be single use battery or may be rechargeable from power supply 842. Power manager 846 controls the supplying of power from power supply 842 and/or battery 844, and the charging of battery 844 if rechargeable. Thus apparatus 800 is powered at all times, unless the combination of power outage and removed or discharged battery occur at the same time. In any event, patient information stored in memory 816 is preserved.

Decoder 820 includes at least a smart tag reader 822 coupled to antenna 824 for reading information from smart tags placed within the detection region thereof. Decoder 820 is coupled to processor 810 for providing information read from a smart tag thereto and optionally for writing information from processor 810 onto a smart tag via antenna 824. Typically, reader 822 is an integrated circuit, such as an I-code reader chip conforming to the ISO 15693 format protocol for wireless RF identification tags, as is available from several commercial sources. Antenna 824 typically operates with reader 822 at 13.56 MHZ and is typically a small antenna suitable for convenient home use, e.g., of the sort shown and described in relation to FIGS. 12A-12B and FIGS. 13A-13C and 14.

Processor 810 can also verify the information read from the medication smart tag utilizing the relational check number described above, and preferably does so. Information read from a medication smart tag by decoder 820, e.g., the medication name, dosage and frequency and/or times of administration thereof, is utilized by processor 810 to schedule times when reminders to take the medication are provided via input/output 830. For a smart tag that has an overwrite protection feature whereby information stored therein may be protected from being overwritten or changed, processor 810 can verify whether such feature is activated, thereby to provide a measure of security.

Input/output functions 830 couple with processor unit 810 for communicating with external apparatus and/or persons, including the patient or other user, i.e. comprise a user interface. Display 834 may be a liquid crystal display (LCD) or other display device for visually presenting information to the patient or other user, e.g., via an LCD panel of 128×64 pixels or larger, and may be illuminated by display lighting 833, e.g., an electro-luminescent (EL) back-lighting device. Illuminated display 833, 834 provides a visual indication helpful for communicating with people who may be hearing impaired, and may provide a display with large font characters and/or high brightness to assist the visually impaired. Display 833, 834 may also produce or include a separate device to produce bright and/or flashing light to serve as an attention getter, warning, alarm and/or reminder, even when the patient or other user is not near the MEDI-TRAKKER™ or MD-HELPER™ device, or is hearing impaired. Display 834 could include a Braille output device for the visually impaired.

Speech synthesizer 835 provides information to a patient or other user in audible form, e.g., speech as well as sounds, and is helpful for communicating information to persons who may not be near the MEDI-TRAKKER™ or MD-HELPER™ device or who may be visually impaired. Speech synthesizer 835 typically comprises an integrated circuit such as the type WS701 circuit available from Winbond, Inc., located in San Jose, Calif., coupled to a sound reproducing device, such as a loudspeaker, piezoelectric device and the like. The speech and/or audible information may be generated by an integrated circuit or may be generated by a software program running on processor unit 810, e.g., stored in memory 816 and executed by processor 812. Speech synthesizer 835 may also produce or include a separate device to produce loud and/or intermittent sound, such as a bell or buzzer sound and the like, to serve as an attention getter, warning, alarm and/or reminder, even when the patient or other user is not near the MEDI-TRAKKER™ or MD-HELPER™ device Keypad 836 provides means for entering information into apparatus 800, such as entering an inquiry seeking information regarding medication and/or its administration, indicating that a medication and/or treatment has been taken and/or administered, for initiating, setting, changing and disabling alarms and automatic reminders, and the like. Typically, a 3×4, 4×4 or other size numerical keypad, e.g., a telephone touch keypad, is sufficient. Keyboard 836 could include a Braille keyboard or input device for the visually impaired.

Panic button 837 provides a direct means for entering information of a specific type, e.g., for summoning assistance and/or help, either from someone locally (nearby) or remote. Typically, panic button 837 may be a clearly evident separate input device, such as a physical button that is, e.g., large and/or brightly colored (e.g., red), and possible illuminated so as to be easy to find in the dark. Optionally, a panic button 837 may be provided that is separate from the remainder of apparatus 800 (which is typically packaged in a plastic or metal container), and which communicates with apparatus 800 via radio, infrared or other wireless means, or via the electrical wiring. Such panic button 837 may be on a pin or necklace that may be worn by the patient or other user, and so may be useful for calling for help in an emergency or other situation when the person cannot reach apparatus 800 to activate a panic button 837 thereon. In either arrangement, panic button 837 cooperates with processor 812 for activating communication with a location remote from apparatus 800, e.g., by telephone, wireless communication to a cordless telephone, cellular telephone and/or via the Internet.

To this end, input/output 830 includes an interface device 831 and a wireless transmitter 832 for wireless communication to a location remote from apparatus 800. Typically, interface 831 is a standard RS232 interface integrated circuit and wireless transmitter 832 is an RS232 wireless transmitter and antenna, e.g., operating at 900 MHZ, to communicate with a wireless receiver within its communication range. This allows communication in event of an emergency (e.g., a fall, seizure, attack or other medical event) or if a patient fails to indicate to apparatus 800 that a medication has been taken or a treatment administered within a predetermined time period, e.g., within an hour of an indicated time.

Such communication could be to a care giver at the same or a nearby location, or to a neighbor, relative or other care giver, or to a doctor, nurse, police, fire, ambulance or other emergency personnel at a remote location. In any event, the recipient may be communicated to via a telephone call, and/or may have a receiver unit similar to wall unit 850 for receiving wireless signals from unit 800 and producing an appropriate signal, alarm, notice, warning and the like, e.g., utilizing devices like display 833, speech synthesizer 835 as described above. Communication to a central computer, server or other computer or an Internet connection is not necessary to the operation of apparatus 800, although such communication could optionally provide access to larger and more sophisticated medical and other databases of information.

Wall adapter 850 includes a wireless receiver 852, typically an RS232 wireless transmitter and antenna, e.g., operating at 900 MHZ, to communicate with wireless transmitter 832. Operation at 900 MHZ is convenient because many household devices (such as cordless/wireless telephones) operate in this frequency band making integrated circuit transmitters, receivers and transmitter/receivers readily available at low cost. Wall unit 850 includes an MCU 854 which couples signals from receiver 852 to dial tone modulation frequency (DTMF) device 856 which initiates telephone dialing with telephone line 858 and communicates information from MCU 854 thereto once connection is established. Communication via telephone line 858 can be to a telephone, a cellular telephone, a cordless telephone, an automatic response device or service and/or via the Internet.

Because apparatus 800 can connect to the Internet via telephone line 858 of wall adapter 850, information can be received by and/or downloaded to apparatus 800 as well as sent or transmitted thereby. For example, information concerning the specific medication, medical device and the like can be downloaded from the dispensing pharmacy, hospital or other provider, and so may be compared by processor 810 with information read from the medication smart tag, e.g., for verification. In the event that the dispenser does not utilize a medication smart tag, the downloaded information can be utilized by apparatus 800 to at least provide reminders to administer medication and/or treatment as well as of times and dosages thereof, and can also warn of possible hazards such as drug interactions and/or allergies.

Power for wall adaptor 850 is provided by AC/DC converter 859 from electrical power drawn from telephone line 858 and/or from a nearby electrical outlet (not shown), and may also include a battery for providing power when power is not available from either telephone line 858 or a wall outlet, so as to allow communication in times of power failure. Thus, power unit 859 may be similar to power unit 840 described above.

Wireless transmitters and receivers 832, 852 may be type SP3223 available from SIPEX located in Billerica, Mass., or type NRF903 available from Nordic VLSI ASA, located in Oslo Norway. MCU 854 may be a small MCU such as the type 8051F300 available from Cygnal Integrated Products, Inc., located in Austin, Tex., and DTMF may be a type CMX867 available from CML Consumer Products, located in Ltd. Essex, England.

Figure 10A:
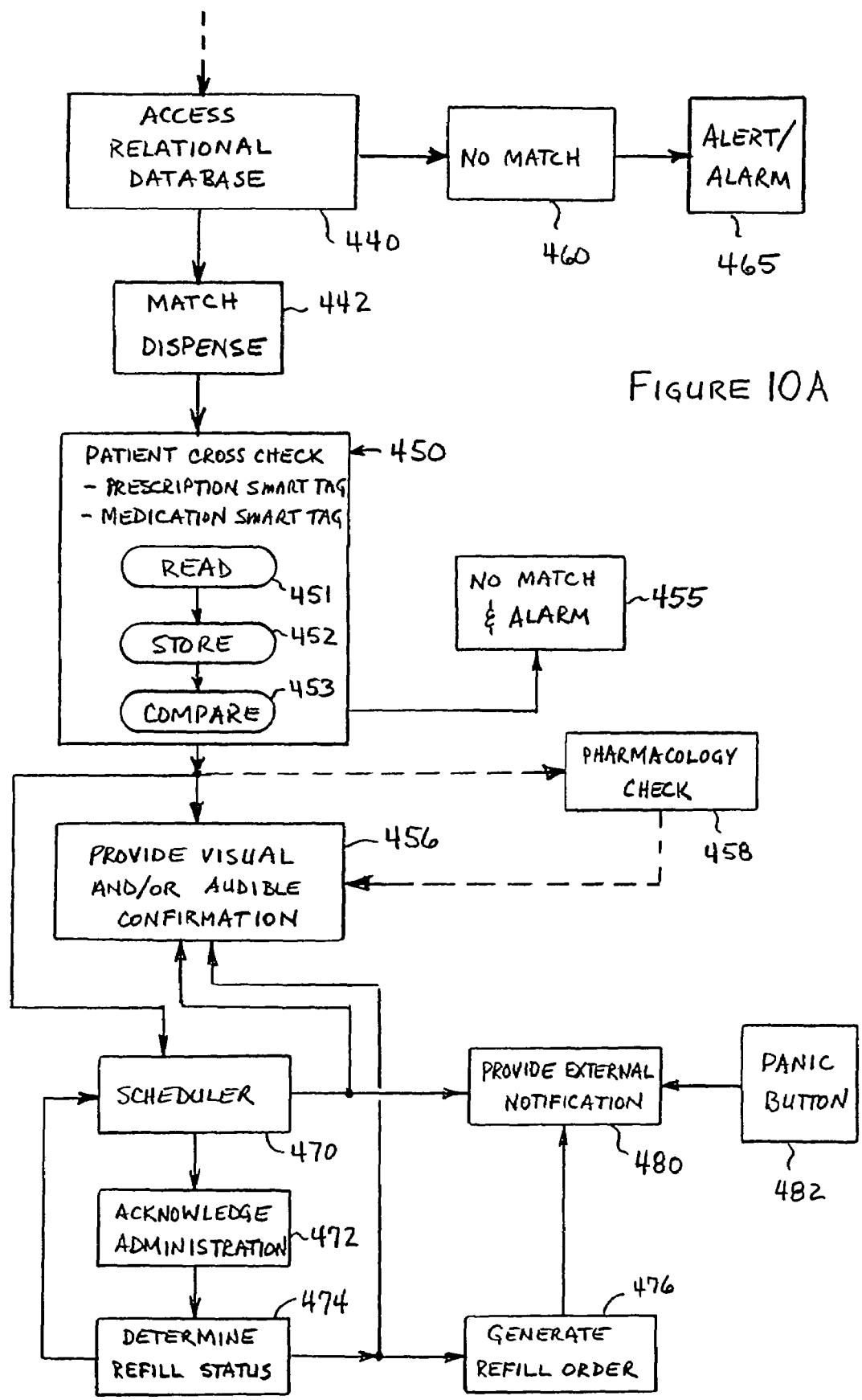
FIGS. 10A and 10B are schematic flow diagrams illustrating aspects of the method of FIG. 8 in context with the medical tracker apparatus of FIG. 9.

FIG. 10A is a schematic flow diagram illustrating additional aspects of the method of FIG. 8 in context with medical tracker apparatus 800 of FIG. 9. If the patient has both the prescription smart tag and the medication smart tag, both are read 451 by the MEDI-TRAKKER™ or MD-HELPER™ device, the information read is stored 452 and is compared and cross checked 450, 453 for consistency, and if not consistent (matching), an alarm is provided 455 as above. If the patient has only the medication smart tag, i.e. has the medication container including a smart tag storing information relating to the medication therein, the information is read 451 and is stored 452, but is not compared 453. A visual confirmation of the information read 451 is displayed 456 of a readout device, such as an LCD display, and/or the information read 451 is provided 456 in audible form, such as by recorded or synthesized speech Thus, the medical information including such information as medication, quantity, dosage, frequency of administration, conditions of administration, refills authorized, physician and/or pharmacy identification and/or contact information, and the like, is stored 452 in the memory of the MEDI-TRAKKER™ or MD-HELPER™ device.

Optionally, but preferably, the MEDI-TRAKKER™ or MD-HELPER™ device includes a database of basic pharmacological information, e.g., drug interaction, proper dosage and frequency ranges, allergies, and the like, utilized to perform a pharmacological check 458, the result of which is also provided 456 visually and or audibly, at least if any adverse or unusual condition or interaction is identified. Serious adverse indications could be utilized to initiate external notification 480, e.g., of a relative, neighbor, care giver, or other appropriate person.

Information read 451 and stored 453 for each medication smart tag read is utilized for scheduling 470 the times when medication and/or treatment is due to be administered and for providing 456 a reminder thereof, i.e. audibly and/or visually. In particular, the medication name, dosage and frequency and/or times of administration thereof are utilized to schedule times when reminders to take the medication are provided. If the medication is taken and is acknowledged 472, e.g., by pressing an acknowledgment button and/or placing the medication into the detection region of the MEDI-TRAKKER™ or MD-HELPER™ device, the indication is recorded, the quantity of medication is adjusted and its refill status determined 474.

Determining refill status includes considering the quantity of medication remaining and the frequency of administration to determine when to provide 456 a reminder to order a refill and considering whether another refill is authorized to determine when to provide a reminder to seek a renewal from the ordering physician. Optionally, where the MEDI-TRAKKER™ or MD-HELPER™ device includes a suitable processor and programming, a refill order can be generated 476 and external notification thereof provided 480, e.g., via the telephone dialer feature of the MEDI-TRAKKER™ or MD-HELPER™ device or via the Internet.

The administration acknowledgment 472 and determined 474 refill status is communicated to the scheduler 470 and if action is not taken within a predetermined time, external notification can be provided 480 as above. Similarly, if the administration of one or more medications is erratic, or if a number of administrations are missed, scheduler 470 could provide 456 a reminder, an alarm and/or an external notification 480, depending upon the extent and duration of the departure from the scheduled administration or upon an absolute condition, as may be programmed. Where it appears that the wrong medication has been taken or that the frequency of administration is other than as read 451 from the medication smart tag, an alarm or warning and/or external notification 480 can be provided 456.

Such predetermined time will depend upon the event scheduled, e.g., for medication that is critical to continued health, missing an administration by an hour or two could be cause for providing external notification 480, while for comfort medication such as pain relief, there might be no time for providing 480 external notification so long as other administrations are reasonably timely. For many medications taken daily where one missed administration may not be immediately dangerous, such as an anti-hypertensive, a diuretic, a cholesterol controller and the like, a 24 hour time might be utilized. Regarding refilling and or renewing prescriptions 474, ignoring an initial reminder or two might not prompt external notification 480, however, as the time to exhaustion of the medication approaches, external notification may be provided 480 if the medication is important to health and well being, but may not be provided for a comfort medication.

In addition, assistance may be summoned by activating a panic button 482 feature that initiates an immediate external notification 480 t the appropriate care giver or provider of assistance. The recipient of external notification 480 need not be the same under all conditions that provide 480 external notification, for example, a missed dose of daily medication might prompt notification 480 of a neighbor, friend or relative, while the missing of a critical medication might prompt notification 480 of a nurse or other skilled responder, and the activation of the panic button 482 might prompt the notification 480 of the police or first aid squad, either initially or if not reset within a predetermined time.

Thus, the apparatus and method described can provide automatic reminders to take medication and/or to give warning when medication is taken improperly, e.g., in time, frequency and/or amount.

Figure 10B:
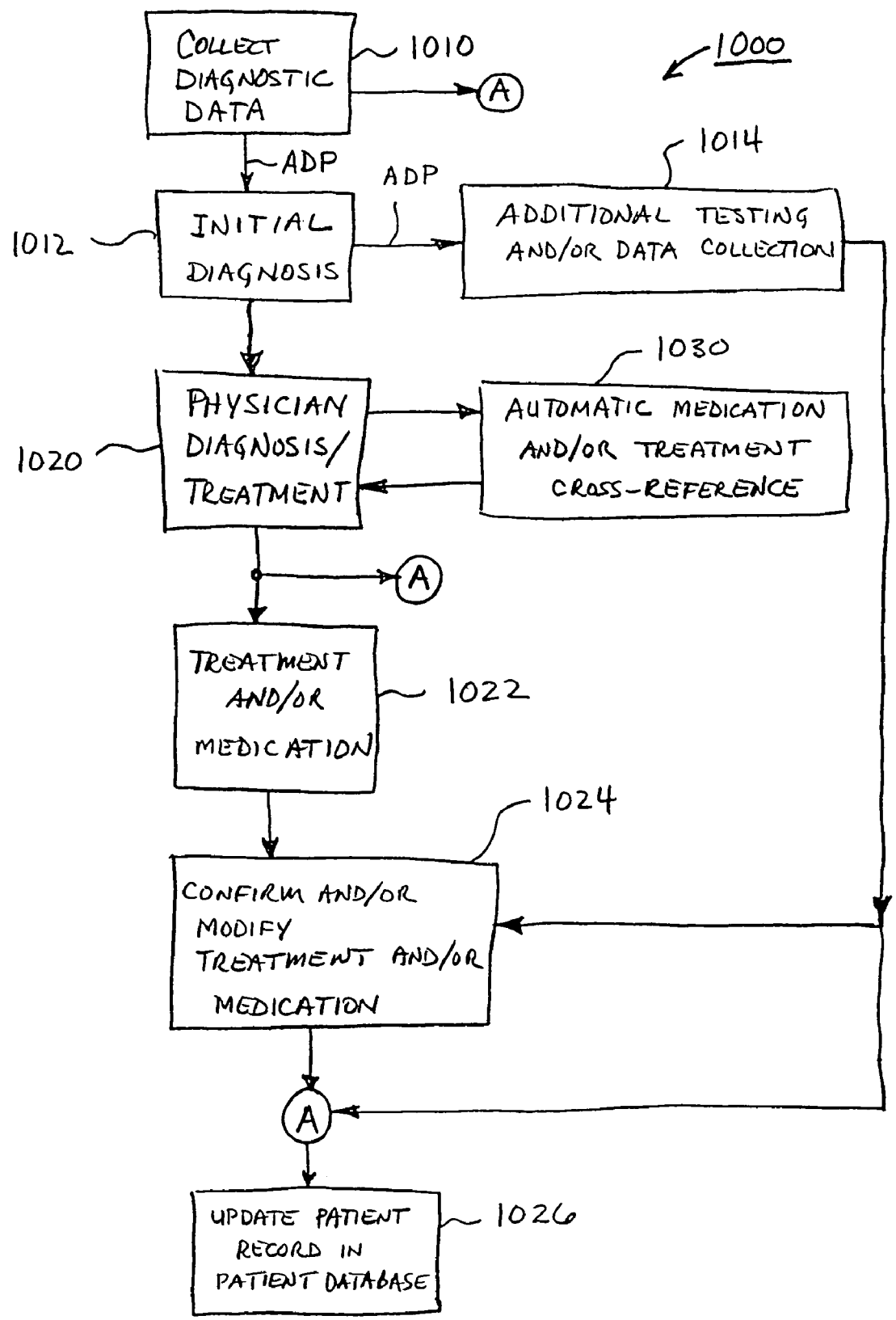

FIG. 10B is a schematic flow diagram illustrating a medical information aspect 1000 of the method of FIG. 8 in context with medical tracker apparatus 800 of FIG. 9, and/or such aspect in the context of the arrangements described above in relation to FIGS. 1, 7 and/or 10A. Diagnostic data is collected 1010 concerning a patient, e.g., information such as identity, age, height, weight, sex, race, family and genetic data, medical history, physical handicaps, known medical conditions, known medical allergies, and current ailment conditions such as symptoms, duration, temperature, blood pressure, pulse rate, blood test data, urine test data, physician observations and the like, at a current time and/or at various times, and is entered into a computer or other processor.

An Automated Diagnostic Program (ADP), i.e. software operating in conjunction with the computer or other processor, includes medical diagnostic information generated from medical testimonies, medical texts, standard treatment protocols, and the like for providing and/or identifying one or more ailments and/or conditions that correspond with the indicated patient information. An initial diagnosis 1012 is provided by the ADP software for review and use by the physician in making a diagnosis 1020 and/or ordering a treatment and/or medication 1020. Typically, the initial diagnosis presented by the ADP software may identify one or more particular conditions and/or diseases or groups of conditions and/or diseases that are likely or possible in view of the available information, e.g., presented in order of likely probability of being correct.

In addition, or alternatively if insufficient information is available for making an initial diagnosis, the ADP software may also indicate and/or recommend additional testing and/or data collection and/or observations 1014 that might be useful in diagnosing and treating and/or in further diagnosing and treating the patient and/or in refining and/or verifying an initial or other diagnosis and/or treatment. Additional tests 1014 recommended may be presented as one or more groups or batteries of one or more tests each, e.g., in order of likely importance.

Typically, the physician initial or tentative diagnosis and/or treatment 1020, 1022 may include the most probable ailment and the prescribed treatment protocol and medication as determined by the physician assisted by information from the ADP software.

Optionally, but preferably, the ADP software automatically cross references 1030 the treatment and/or medication prescribed by the physician 1020 with medical information for identifying indications and contraindications therefor. Examples of such cross references may include cross referencing prescribed medications to an NDC or other medication database for checking for appropriateness, effectiveness, contraindications, alternatives, drug interactions, expected benefits and/or side effects, possible allergic reactions, specific patient allergies, and the like.

If the cross reference 1030 confirms the appropriateness of the treatment and/or medication, treatment and/or medication 1022 as prescribed by the physician is administered to the patient. If not, the physician may continue diagnosing, with or without assistance from the ADP software, until satisfied with a diagnosis and treatment and/or medication, and then the treatment and/or medication 1022 as prescribed by the physician is administered to the patient. Treatment 1022 may include, for example, one or more of the giving of one or more medications, the administration of one or more treatments and/or tests, the making of observations and/or the collecting of patient and/or treatment data.

In response to the additional testing and/or data collection 1014, and/or to observations made by a physician and/or other medical personnel in the course of treatment and/or medication 1022, the treatment and/or medication may be confirmed and/or modified 1024, including any or all of the aspects thereof set forth above.

Optionally, but preferably, the diagnostic and other data 1010 collected from the patient and/or examination and/or interview is stored 1026 in a patient record in a patient database, wherein at the initial collection 1010 the patient data record is established for that patient in the patient database and the patient record is thereafter updated 1026 by the addition to and/or modification of the patient information stored therein. Examples of times at and during which data may be collected and/or otherwise obtained include, e.g., the collection of diagnostic data 1010, the additional testing and/or data collection 1014, the physician diagnosis and/or treatment 1020, and/or the confirming and/or modifying of treatment and/or medication 1024.

It is noted that all or part of medical information aspect 1000 may be associated with any one or more of the embodiments described herein. For example: The reading 140 and comparing 150 of information from a smart tag and the searching a relational database 190 described in relation to FIG. 1 may include steps 1010, 1012, 1014, 1030, 1022 (as to dispensing medication and/or a medical apparatus), 1024, and/or 1026. The comparing of patient information and medical information either directly or via a communication link 340, 345 to a relational database described in relation to FIG. 7 may include steps 1010, 1012, 1014, 1030, 1022 (as to dispensing medication and/or a medical apparatus), 1024, and/or 1026; the generating of a patient treatment history described in relation to FIG. 7 above may include steps 1010, 1014, 1030, 1022 (as to medication and/or a medical apparatus dispensed and/or administered), 1024, and/or 1026. The comparison with a relational database and medical information database 440 and/or the cross checks 430, 450 described in relation to FIG. 8 above may include steps 1010, 1012, 1014, 1030, 1022 (as to dispensing medication and/or a medical apparatus), 1024, and/or 1026. The and/or the cross check 450 and/or pharmacological check 458 described in relation to FIG. 10A above may include steps 1012, 1014, 1030, 1022 (as to medication and/or medical apparatus), 1024, and/or 1026.

Figure 11A:
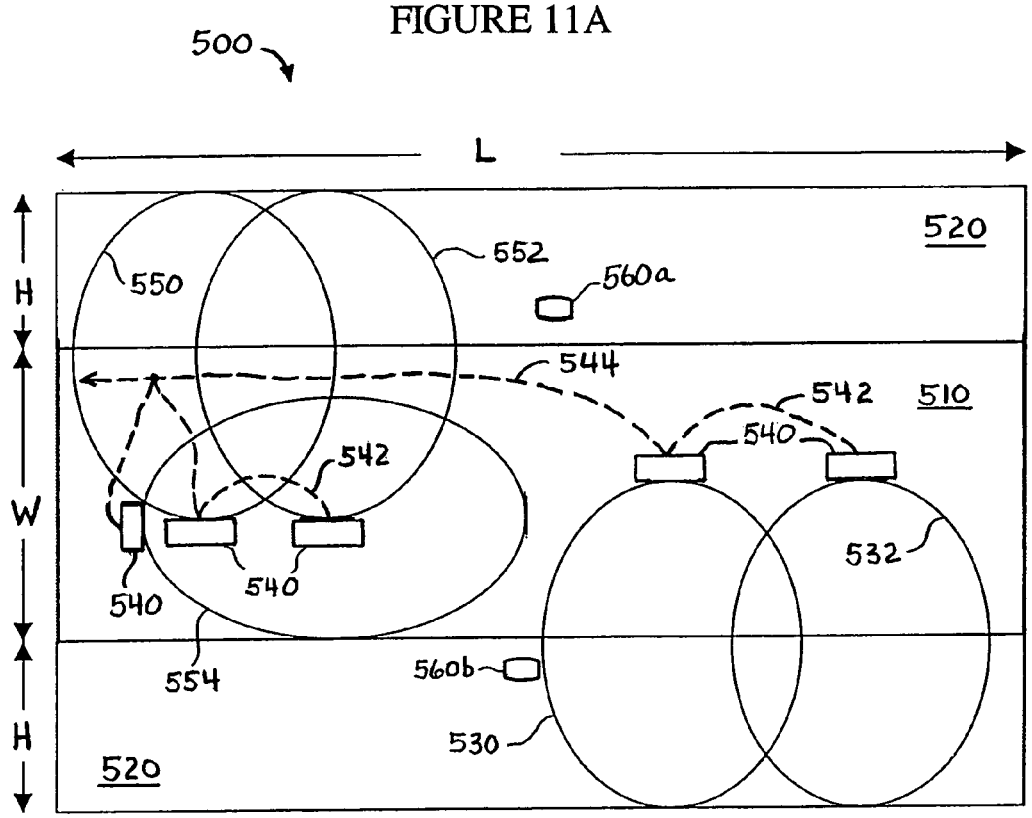
FIGS. 11A and 11B are an unfolded view and an isometric view, respectively, of an example open antenna array arrangement.
Figure 11B:
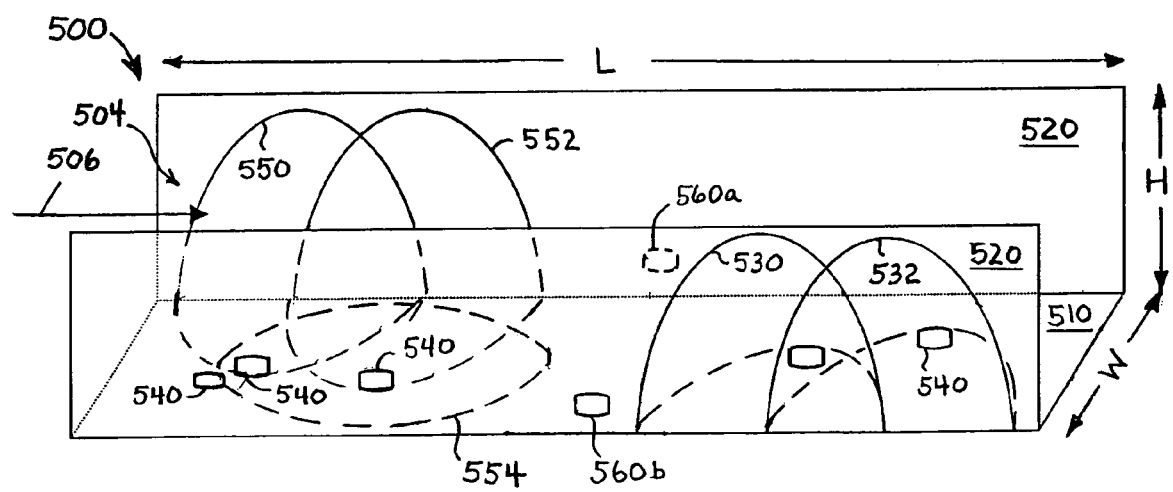

FIGS. 11A and 11B are an unfolded view and an isometric view, respectively, of an open or trough antenna array arrangement 500. Open antenna array 500 includes three panels, e.g., a bottom or center panel 510 and two spaced apart side panels 520 contiguous thereto, wherein the two side panels 520 are typically positioned perpendicular to center panel 510, but may be at a greater or lesser angle, if convenient or desired. For example, the angle between adjacent panels may be between about 80° and about 100°. FIG. 11A is an "unfolded" view in that panels 520 are illustrated in a plane with center panel 510, rather than perpendicular thereto as in the position in which they are utilized. The designations "bottom" and "side" are examples in that antenna array 500 may be utilized in any desired orientation. For example, the side called "bottom" may be positioned at the top or a side depending upon the need and/or convenience in a particular application or environment, e.g., so as to allow a "tall" or "wide" object to pass without hindrance.

Panels or planes 510, 520 define an open passage or trough 504, i.e. a detection region, through which articles may pass (e.g., in the direction indicated by arrow 506) or in which articles and/or objects may be placed for detecting wireless tags (smart RFID tags) thereon, as described above. The passage 504 is described as "open" because it is not enclosed on four sides, as is the case, for example, for antenna arrays 10, 10', 10", 10*a* and 10*p* of FIGS. 2, 3, 4, 5A and 5B. An open passage or trough is convenient and may be desirable because it facilitates its installation, e.g., in locations with pre-existing conveyors, allows for passage of an article having a height greater than the height of the passage, and makes manual retrieval of any article therein easier and safer.

For example, antenna array 500 may be installed in or removed from an operation position in which a conveyor moves articles having wireless tags through passage or trough 504 thereof without having to remove the conveyor, as is the case with a closed or "tunnel" type of antenna array wherein the conveyor must traverse an enclosed passage. Installation and removal of antenna array 500 may be further facilitated where panels 520 are either hinged to panel 510 and/or are detachable therefrom, and such arrangement also eases transport.

Typically, antenna array 500 is disposed with center panel 510 at bottom with a conveyor passing through passage 504 parallel and proximate to panel 510 and with side panels 520 extending upwardly on either side of the conveyor. For an example baggage conveyor, such as may be utilized at an airport or railroad station, array 504 may have a length L of about 60-80 inches (about 1.5-2 meters), a width W of about 36-43 inches (about 0.9-1.1 meters) and a height H of about 25-30 inches (about 0.63-0.76 meters), thereby to accommodate a 1 meter wide conveyor belt, although other dimensions may be utilized for other applications of array 500.

Example antenna array 500 includes five loop antenna 530, 532, 550, 552, 554, each of which is coupled by a tuning circuit, matching network and/or filter 540 (e.g., similar to tuning network or filter 36 described above) to a wireless article reader/decoder (e.g., similar to reader/decoder 50, 150, 160 described above). The loops of antenna 530 and 532 extend to proximate the edge of panel 520 and are partially overlapping, e.g., with about 10-40% of the area being overlap, and are disposed on both bottom panel 510 and one of panels 520, e.g., with about 20-70% of the area on one panel. Similarly, the loops of antenna 550 and 552 extend to proximate the edge of other panel 520 and are partially overlapping, e.g., with about 10-40% of the area being overlap, and are disposed on both bottom panel 510 and the other one of panels 520, e.g., with about 20-70% of the area on one panel. In addition, the loop of antenna 554 is disposed on panel 510 and overlaps each of loop antenna 550, 552, e.g., by about 10-35%.

In one example antenna array 500 suitable for detecting wireless tags associated with baggage, as might be utilized in an airport or rail station, array 500 is 79 inches long, 43 inches wide and 29 inches high (about 2.0 by 1.1 by 0.74 meters). The structure of panels 510, 520 is provided by a "U-shaped" frame of tubular members (e.g., plastic pipe covered with a plastic netting to which antenna 520-552 are fastened) Each of loop antenna 530, 532, 550, 552 is generally elliptical in shape and has a minor diameter of about 22 inches (about 0.56 meter) and a major diameter of about 40 inches (about 1.02 meter) of which about 29 inches (about 0.74 meter) is on a panel 520 and about 11 inches (about 0.28 meter) is on panel 510. Of the 22 inch minor diameter (about 0.56 meter), about 8 inches (about 0.2 meter) overlaps the nearest like loop antenna The exact percentage of overlap may vary depending upon the shape and mutual coupling of the loop antenna to produce a near-field effect of mutual non-canceling fields in all three mutually orthogonal directions.

The loop antenna 530-554 of antenna array 500 may operate in parallel (i.e. simultaneously) via connections provided by coaxial cables and coaxial connectors, e.g., Tee connectors and cable connectors of the BNC type. Appropriate tuning, isolation and decoupling is provided by tuning and matching circuits 540, and by selecting an appropriate length for the interconnecting coaxial cable, e.g., about 14 inches (about 0.36 meter) between overlapping antenna 530-532 and 550-552. Typically, each antenna 530-554 is first tuned with its associated matching-filtering network 540, e.g., by adjusting variable tuning capacitors thereof. After the antenna 530-554 are connected by 50-ohm coaxial cables and BNC Tee connectors, they are re-tuned and matched for satisfactory read-write distances in each of the x, y and z directions for the respective panels 510, 520. Interactions between the fields produced by each loop antenna 530-554 necessitates such adjustment using the variable tuning capacitors included in each of tuning/matching circuits 540.

Alternatively, antenna 530-554 may be switched and/or sequenced in time, although simultaneous operation is presently thought to be preferable.

Thus, loop antenna 530-554 cooperate to establish electromagnetic fields within detection region 504 of sufficient field strength to communicate with wireless tags at a predetermined frequency, e.g., with substantially 100% reading accuracy independent of the orientation and position of the tag within passage 504.

One preferred example wireless tag useful with antenna 500 in a baggage tracking application operates at about 13.56 MHZ and has a spiral antenna about two inches by three inches in size. Tuning circuits 540 couple and tune antennas 530-554 to communicate with a wireless article reader/writer that operates at about 13.56 MHZ, typically at an average power level of about 4 watts or less, however, greater power may be utilized for larger antenna arrays. Wireless tags, readers/writers and antenna that operate and communicate at other frequencies may also be utilized.

Figure 12A:
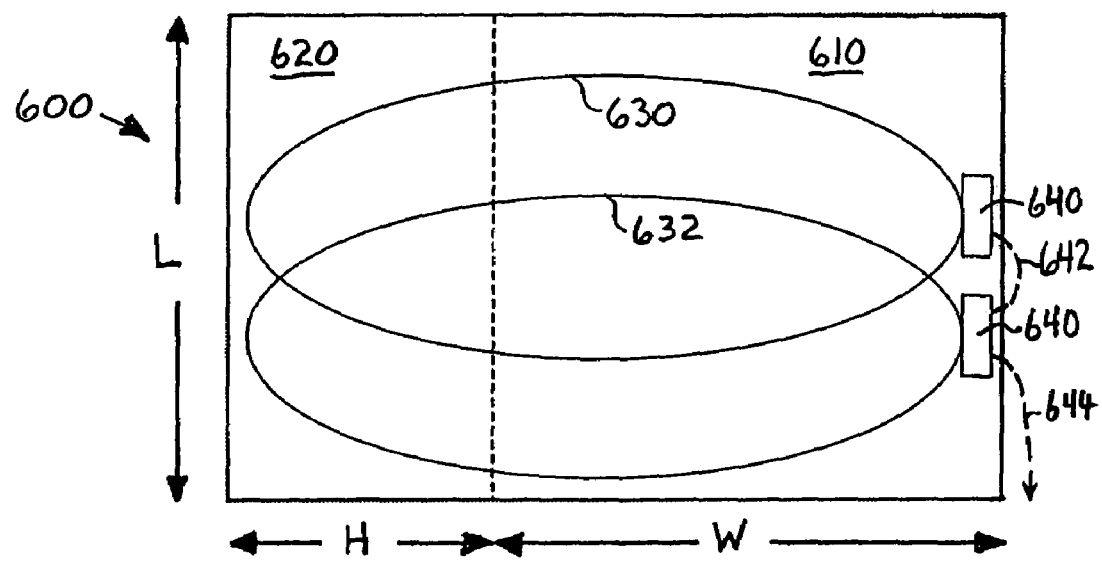
FIGS. 12A and 12B are an unfolded view and an isometric view, respectively, of an example open antenna array arrangement.
Figure 12B:
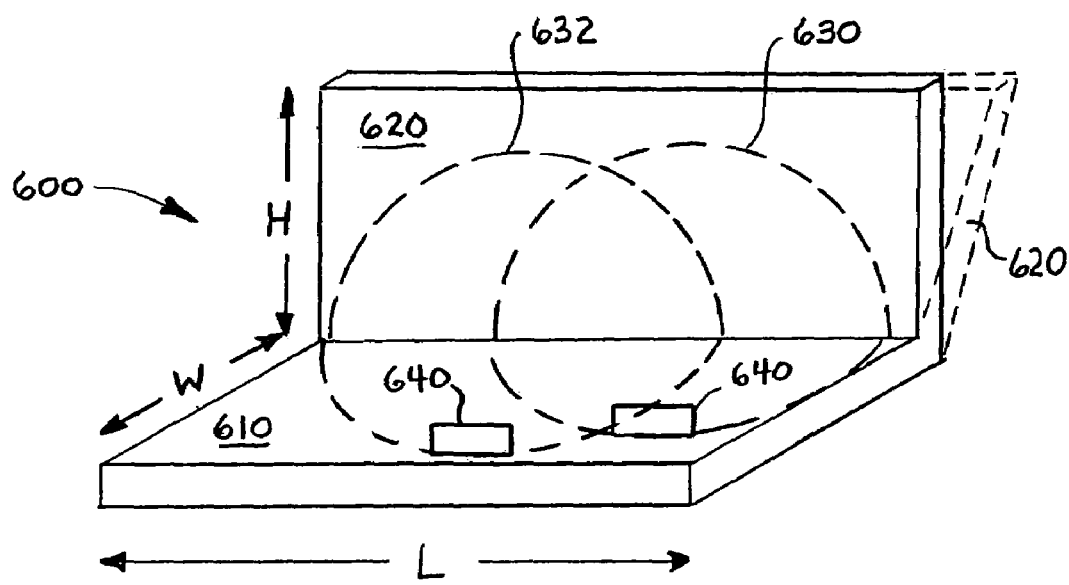

FIGS. 12A and 12B are an unfolded view and an isometric view, respectively, of an open antenna array arrangement 600. Open antenna array 600 includes two panels, e.g., a bottom or base panel 610 and a vertical or side panel 620 contiguous thereto, wherein the side panel 620 is typically positioned perpendicular to base panel 610, but may be at a greater or lesser angle, if convenient or desired. For example, the angle at which the two panels are disposed may be between about 80° and about 100°. FIG. 12A is an "unfolded" view in that panel 620 is illustrated in a plane with base panel 610, rather than perpendicular thereto as in the position in which they are utilized. The designations "bottom" and "base," and "vertical" and "side," are examples in that antenna array 600 may be utilized in any desired orientation.

Panels or planes 610, 620 define an open passage or detection region 604 therebetween through which articles may pass or in which articles and/or objects may be placed for detecting wireless tags (smart RFID tags) thereon, as described above. An open passage or region is convenient and may be desirable because it facilitates its installation, e.g., in locations with pre-existing conveyors, allows for detection of an article having a size greater than the size of the detection region and makes manual placement and retrieval of any article therein easier and convenient.

For example, while antenna array 600 may be installed in or removed from an operation position in relation to a conveyor as described above, it is thought to be suited for use where a person or machine places articles having wireless tags into the detection region 604 thereof. Typically, antenna array 600 is placed on a counter, table or other horizontal surface with panel 610 at bottom and with side panel 620 extending upwardly. Alternatively, antenna array may be mounted to a wall, cabinet or other vertical surface with base panel 610 extending therefrom For an example in dispensing of relatively small objects, such as may be utilized at a pharmacy or hospital for dispensing medication and/or medical devices, array 604 may have a length L of about 38 inches (about 0.97 meter), a width W of about 10-30 inches (about 0.25-0.76 meter) and a height H of about 26 inches (about 0.13-0.38 meter), although other dimensions may be utilized for other applications of array 600.

Example antenna array 600 includes two loop antenna 630, 632, each of which is coupled by a tuning circuit, matching network and/or filter 640 (e.g., similar to tuning network or filter 36 described above) to a wireless article reader/decoder (e.g., similar to reader/decoder 50, 150, 160 described above). The loops of antenna 630 and 632 extend to proximate the edges of panels 610, 620 and are partially overlapping, e.g., with about 10-40% of the area being overlap, and are disposed on both panel 610 and panel 620, e.g., with about 20-70% on one panel.

The loop antenna 630-632 of antenna array 600 may operate in parallel with appropriate isolation and decoupling provided by tuning circuits 640, i.e. simultaneously as above, and/or may be switched and/or sequenced in time. Thus, loop antenna 630-632 cooperate to establish electromagnetic fields within detection region 604 of sufficient field strength to communicate with wireless tags (RFID tags) at a predetermined frequency, e.g., with substantially 100% reading accuracy independent of the orientation and position of the tag within detection region 604.

One preferred example wireless tag useful with antenna 600 operates at about 13.56 MHZ and has a spiral antenna about two inches by three inches in size. Another preferred example wireless tag useful with antenna 600 in dispensing medication in relatively small containers operates at about 13.56 MHZ and has a spiral antenna about 0.5 inches by 0.6 inches in size. Tuning circuits 640 couple and tune antennas 630-632 to communicate with a wireless article reader/writer that operates at about 13.56 MHZ, typically at an average power level of about 4 watts or less.

The described arrangement is suitable for wireless tags and readers/decoders operating at frequencies near 13.56 MHZ for producing a suitable near-field effect for reading information from the wireless tag and for transmitting signals information thereto. Antenna array 600 may be small, e.g., about 4 by 4 by 4 inches (about 0.10 by 0.10 by 0.10 meter) or less, depending upon the strength of the fields produced at the operating frequency, e.g., 13.56 MHZ. Wireless tags, readers/writers and antenna that operate and communicate at other frequencies may also be utilized.

It is noted that antenna 500 and/or antenna 600 may be fabricated and/or shipped "flat" and then be "folded" into the trough or "L" shape configuration at a test and/or use location or may be fabricated and/or transported in the trough or "L" shape configuration. The coaxial cable of which antenna 500, 600 are preferably made may be formed and attached to a structure and/or frame defining the trough and/or "L" shape either as part of fabrication of antenna 500, 600 or at a test and/or use location.

Loop antenna array 500 (and/or 600) may include a light or infrared source and detector pair 560a, 560b for detecting objects passing through the detection region 504 thereof. The light and/or IR beam between source/detector pair 560a, 560b will be broken or interrupted by an object passing therethrough to provide an independent signal that may be correlated with detection of a wireless article and/or RFID tag associated with the object passing therethrough, and so may be utilized for providing an independent check or confirmation that the object is tagged and that the wireless tag has been detected via antenna 500. Such check or confirmation may be utilized in testing and/or evaluating antenna array 500, and/or in operating antenna array 500. Pair 560a, 560b could be connected to a counter and/or to an alarm e.g., as for detecting untagged or improperly tagged baggage that may pose a security and/or accounting issue to be investigated and/or resolved, and/or to alert an appropriate person of such situation or possible non-detection.

FIGS. 13A and 13B are isometric views of example embodiments of open antenna array 700, 700' and FIG. 13C is a view of the bottom of the example antenna array 700 of FIG. 13A. Example antenna 700 is of generally rectangular shape and has four sides or walls 712, 714, 716, 718 extending from a bottom or base 710, thereby to define a generally rectangular opening or detection region 704 into which an object including an RFID tag or wireless tag may be placed to be identified and/or detected by electromagnetic fields coupled via loop antenna 720.

Example antenna array 700' of FIG. 13B is like antenna array 700 except that its wall(s) 712-718 define a generally circular or elliptical or oval shape. In fact, wall(s) 712-718 may be arranged to define any desired shape of container. Antenna arrangements 700, 700' may be particularly useful with medication containers, medical devices, and the like, that are tagged or associated with a wireless identification tag, e.g., in a hospital, pharmacy and/or home or use environment.

Loop antenna 720 is disposed in a meandering or serpentine fashion on sides 712, 714, 716, 718 and base 710 generally as illustrated. Specifically, loop antenna 720 has a fixed wavy or undulating shape, e.g., defines a generally wavy or sinusoidal-like shape 722, 724, 726 on each of sides 712, 714 716, respectively, being proximate base 710 near the intersections of sides 712, 714, 716, 718 and distal base 710 at an intermediate region of each of sides 712, 714, 716. Loop antenna 720 is disposed in a "pretzel-like" shape 728 on base 710 wherein loops 728a, 728b, 728c are defined by the cable of loop 728 of antenna 720 crossing over itself, e.g., three times. Loop antenna 720 couples to tuning circuit 740 disposed, for example, on side 718, which couples to an RFID tag reader and/or writer, and/or a processor, computer and/or utilization device or system 750, e.g., as described herein.

Thus, loop antenna 720 has at least two (preferably three) fixed undulating loop portions 722, 724, 726 on the side(s) or wall(s) 712, 714, 716 of container 700, 700' and has at least two (preferably three) loop portions 728 on the bottom or base thereof, thereby defining a detection region 704. Loop antenna 720 is preferably formed of a coaxial cable, e.g., a type RG 174/U coaxial cable, disposed in the pattern described and illustrated, and is preferably enclosed within the wall(s) and base of a container 700, 700'. While the wall(s) 712-718 are illustrated as being generally perpendicular to base 710, they may be at an angle with respect thereto, e.g., between 80° and 100°, typically outwardly so that the opening to detection volume 704 is larger than is base 710.

FIG. 14 is an isometric diagram illustrating the arrangement of the antenna 700 of the example antenna array of FIGS. 13A and 13C. The wall(s)/side(s) 712-718 and base/bottom 710 are illustrated as transparent so that the arrangement of loop antenna 720 is visible. The coaxial cable of antenna 720 includes three undulations 722, 724, 726 and a three loop portion 728a, 728b, 728c all in series and coupled to tuning circuit 740, thereby to define a detection region 704 approximating the volume defined by base and walls 710-718 shown in phantom Container 700, 700' including an antenna 720 comprises a container 700, 700' having a base 710 and a wall 712-718 extending from the base 710 to define a volume 704. Loop antenna 720 has a portion 728 disposed on the container base 710 and crossing over itself at least twice on the container base 710, and a wavy portion 722, 724, 726 disposed on the container wall 712, 714, 716, 718 and defining at least two waves 722, 724, 726 on the container wall 712, 714, 716, 718. A means 740 couples the loop antenna 720 to an external processor 750. The container wall 712, 714, 716, 718 defines one of a circular, oval, elliptical, rectangular and square shape. The coupling means 740 may include at least one of a tuning circuit, a filter and a switch for selectively connecting said loop antenna to the external processor, as described.

With regard to each of the antennas 530-554, 630-632, 720, of FIGS. 11A-11B, 12A-12B, 13A-13C and 14, the arrangement of the matching network and/or tuning circuit 540, 640, 740, is as described above in relation to FIG. 6, it being understood that the values of the various components thereof are selected for the particular antenna and its frequency of operation. Other tuning circuits and/or matching networks may be utilized as is known to those of skill in the art.

It is noted that any one or more of the antenna arrangements 500, 600, 700, may be employed with any MEDI-TRAKKER™ or MD-HELPER™ device or similar apparatus, and/or as any one or more of antenna arrangements 44, 44', 44" described above. While various simultaneously operated and/or temporally and/or spatially separated antenna array arrangements may be utilized with the present invention, other examples of suitable antenna arrays are described in detail in Applicant's co-pending U.S. patent application Ser. No. 09/854,722 entitled "ANTENNA ARRAY FOR SMART RFID TAGS" filed on May 14, 2001.

Antennas that generate electromagnetic fields in each of three mutually orthogonal directions are generally preferred because they tend to be able to read smart tags reliably irrespective of the orientation of the smart tag within the detection region of the antenna arrangement. It is thought that the desirability of rapid 100% or near 100% reading of smart tags tends to be of more importance where many tags are to be read in a relatively shorter time period or where the smart tags are placed into or moved through the detection region mechanically, e.g., on a conveyor, but may be of lesser importance where the reading of smart tags is by individual hand placement, e.g., as is the case for a MEDI-TRAKKER™ or MD-HELPER™ device intended for home or individual use.

It is noted that smart tags may be read and written numerous times and the information therein may be updated and/or otherwise changed at any time and as needed, thereby offering a particular advantage over bar-coded labels. While the arrangements described herein may be utilized with many sizes, varieties and types of wireless tags or smart tags or RFID tags and/or labels and/or cards, suitable wireless tags are described and shown, for example, in Applicant's U.S. patent applications Ser. Nos. 10/191,580 entitled "ELECTRONIC CIRCUIT CONSTRUCTION, AS FOR A WIRELESS RF TAG" filed Jul. 9, 2002, No. 09/412,058 entitled "ARTICLE HAVING AN EMBEDDED ELECTRONIC DEVICE, AND METHOD OF MAKING SAME" filed Oct. 4, 1999, No. 09/411,849 entitled "WIRELESS ARTICLE INCLUDING A PLURAL-TURN LOOP ANTENNA" filed Oct. 4, 1999, and No. 09/671,923 entitled "TAMPER-RESISTANT WIRELESS ARTICLE INCLUDING AN ANTENNA" filed Sep. 28, 2000.

While the present invention has been described in terms of the foregoing example embodiments, variations within the scope and spirit of the present invention as defined by the claims following will be apparent to those skilled in the art. For example, many different combinations of smart tags, antenna, reader/writer units, communication devices and processors may be employed in making and using the system and in practicing the method described herein. Antenna may be provided in any kind of area such as a pharmacy, a hospital, a nursing home, a care facility, a rehabilitation center, a clinic, an office of a doctor, dentist or other health care provider, a home an office or other workplace, a school, a government facility, as well as other places whether or not described herein.

Apparatus providing visual and/or audible notice, alerts, warnings, etc. including those suitable for use by hearing or visually impaired persons, may be provided in apparatus and used in the method herein whether for individual or home use or for use in a large or small hospital, office, clinic or other professional facility.

Smart tags of various types may be utilized as convenient. For example, a smart tag may have a polyimide substrate with solid copper conductors thereon and nickel-gold metal plated interconnection pads, with the electronic chip connected to the interconnection pads with a high-temperature flexible conductive adhesive. Smart tags may be packaged to prevent moisture, chemicals and solvents from reaching and attacking the operating elements of the smart tag.

A smart tag reader/writer, also referred to as a coder, reads information that is stored in a smart tag, e.g., in a memory thereof, and/or writes information to a smart tag for storing the same therein, e.g., to the memory thereof. The reading and writing is sometimes referred to generally as coding, hence a smart tag coder, and may include decoding information that is stored in a smart tag, e.g., in a memory thereof, and/or encoding information into a smart tag for storing the same therein, e.g., to the memory thereof.

In any of the examples described, one or more of the smart tags may be collected, erased and reused. Where a dispenser of medication, or of a medical implement or device is required to keep the original prescription or order therefor, a copy of the prescription or order including the original smart tag or a duplicate smart tag encoded to match the original smart tag may be provided. In another utilization, identification bracelets including smart tags are issued to mother and baby in a hospital or birthing center at the time of birth Each smart tag has related data stored therein for verifying, e.g., at feeding time and/or release, that the mother's and baby's tags match, whereby the mother has the baby born to her.

Optionally, the same information may be both transmitted to the smart tag and stored in its memory and stored in the memory of the tracking station. Thus, both the smart tag and the tracking station have the same information pertaining to that object and that station. Any other desired information may likewise be transmitted and stored in the smart tag. Where plural tags may be present in the smart tag detection region of a station at the same time, conventional smart tag "collision-avoidance" or "anti-collision" techniques are employed.

It should be noted that the tracking stations may include any number and types of locations, as may be necessary, convenient or desirable in the processing, transport and use of any given object. The stations need not be located in proximity to each other, but may be in separate buildings or facilities, at different locations and even widely dispersed geographically, and need not be under the ownership and/or control of any one person or entity.

The smart tags may be adhesive tags that adhere to an object in a way that renders them tamper resistant or may be included in an anti-theft device, such as the relatively large conventional reusable circular anti-theft devices available from Check-Point Systems of Thorofare, N.J., typically utilized in retail clothing stores. These conventional anti-theft devices may be large so as to be obvious and not be removable without damaging the object unless removed using a special tool or release device generally not available to the public. Typically, a smart tag is configured to fit inside such conventional anti-theft device so that the anti-theft-device and the smart tag cooperate to reduce theft and lost or misplaced objects, as would be important where expensive medical devices, implements and medications are in view.

What is claimed is:

1. A method for assisting with any one or more of or any combination of administering a medication, using an implement, using a medical device, administering a treatment and performing a procedure at a point of administration, use, treatment, or performance thereof, the method comprising:

providing a first coded wireless RFID tag associated with a person who is to receive any one or more of or any combination of a medication, an implement, a medical device, a treatment and a procedure;

wherein the first coded wireless RFID tag includes a permanent number and coded data comprising at least an identification of the person with which it is associated and an identification of any one or more of or any combination of a medication, an implement, a medical device, a treatment and a procedure that the person is to receive, and a relational check code representative of the permanent number or of the permanent number and the coded data;

providing a second coded wireless RFID tag associated with each of any one or more of or any combination of a medication, an implement, a medical device, a treatment and a procedure that is to be provided;

wherein each second coded wireless RFID tag includes a permanent number, coded data comprising at least an identification of the medication, implement, medical device, treatment and procedure with which it is associated and a relational check code representative of the permanent number or of the permanent number and the coded data;

reading the respective coded data of the first and second coded wireless RFID tags in conjunction with any one or more of or any combination of the administering a medication, using an implement, using a medical device, administering a treatment and performing a procedure;

processing the relational check codes read from the first and second coded wireless RFID tags for verifying the coded data read therefrom;

comparing data from a computer database that includes data in addition to the respective coded data read from the first and second coded wireless RFID tags with the respective coded data read from the first and second coded wireless RFID tags for matching the any one or more of or any combination of a medication, an implement, a medical device, a treatment and a procedure to be provided with the any one or more of or any combination of a medication, an implement, a medical device, a treatment and a procedure that the person is to receive; and providing, responsive to said comparing, a visual indication, an audible indication, or both, indicating whether the provided any one or more of or any combination of a medication, an implement, a medical device, a treatment and a procedure and the any one or more of or any combination of a medication, an implement, a medical device, a treatment and a procedure that the person is to receive match or do not match, whereby the person that is to receive any one or more of or any combination of a medication, an implement, a medical device, a treatment and a procedure is matched at the point of administration, use, treatment, and/or performance to the any one or more of or any combination of a medication, an implement, a medical device, a treatment and a procedure that is to be provided.

2. The method of claim 1:

wherein the data read from the first coded wireless RFID tag includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, physician information, insurance, an illness, a disease, a condition, a name of a medication, a dosage of a medication, a frequency of administration of a medication, a prescribing person, and a condition treated; and wherein the data read from the second coded wireless RFID tag includes any one or more of or any combination of a name of any one or more of or any combination of a medication, implement, medical device, treatment, and procedure, a dosage, a frequency of administration, a lot identification, an NDC number, an expiration date, a manufacturer, a prescribing person, a dispenser, physician information, insurance, a facility, a surgical operating room, a diagnostic machine, an illness, a disease, a condition, drug interaction information, allergic reaction information, drug treatment information, drug overdose information, contraindication information, expected benefits, side effects, and inappropriate administration information.

3. The method of claim 1 wherein the data from the computer database includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, insurance, an illness, a disease, a condition, a name of a medication, a dosage of a medication, a frequency of administration of a medication, a lot identification, an NDC number, an expiration date, a manufacturer, a prescribing person, physician information, a facility, a surgical operating room, a diagnostic machine, a dispenser, a number of refills, a condition treated, drug interaction information, allergy information, allergic reaction information, drug treatment information, drug overdose information, contraindication information, alternative treatments, expected benefits, side effects, patient information, an NDC database information, a medication database information, and inappropriate drug administration information.

4. The method of claim 1:
wherein said comparing data from a computer database includes accessing a computer relational database via communication means including any one or more of wire, cable, optical fiber, local area network (LAN), wide area network (WAN), radio transmission, optical transmission, the Internet, or any combination thereof; or
said method further comprising accessing a computer relational database via communication means including any one or more of wire, cable, optical fiber, local area network (LAN), wide area network (WAN), radio transmission, optical transmission, the Internet, or any combination thereof or
both of the foregoing.

5. The method of claim 4 wherein the relational database includes any one or more of or any combination of an open database to which information can be added, deleted, and changed, a closed database not allowing information to be added, deleted or changed via the communication means, an NDC database, a medication database, and an automated diagnostic program.

6. The method of claim 1 further comprising providing a label associated with or affixed to the any one or more of or any combination of a medication, an implement, a medical device, a treatment and a procedure, wherein the label includes in human readable form at least a portion of the data coded in the first or second coded wireless RFID tag that is associated with the any one or more of or any combination of a medication, an implement, a medical device, a treatment and a procedure.

7. A method for assisting with any one or more of or any combination of administering a medication, using an implement, using a medical device, administering a treatment and performing a procedure at a point of administration, use, treatment, or performance thereof, the method comprising:
providing a coded wireless RFID tag associated with a person who is to receive any one or more of or any combination of a medication, an implement, a medical device, a treatment and a procedure;
wherein the coded wireless RFID tag includes a permanent number, coded data comprising at least an identification of the person with which it is associated and an identification of any one or more of or any combination of a medication, an implement, a medical device, a treatment and a procedure that the person is to receive, and a relational check code representative of the permanent number or of the permanent number and the coded data;
reading the coded data of the coded wireless RFID tag in conjunction with any one or more of or any combination of the administering a medication, using an implement, using a medical device, administering a treatment and performing a procedure, and a relational check code representative of the coded data;
processing the relational check code read from the coded wireless RFID tag for verifying the coded data read therefrom;

comparing data from a computer database that includes data corresponding to the coded data read from the coded wireless RFID tag and includes data in addition to the coded data read from the coded wireless RFID tag with the respective coded data read from the coded wireless RFID tag for matching the any one or more of or any combination of a medication, an implement, a medical device, a treatment and a procedure to be provided with the any one or more of or any combination of a medication, an implement, a medical device, a treatment and a procedure that the person is to receive; and
providing, responsive to said comparing, a visual indication, an audible indication, or both, indicating whether the provided any one or more of or any combination of a medication, an implement, a medical device, a treatment and a procedure and the any one or more of or any combination of a medication, an implement, a medical device, a treatment and a procedure that the person is to receive match or do not match,
whereby the person that is to receive any one or more of or any combination of a medication, an implement, a medical device, a treatment and a procedure is matched at the point of administration, use, treatment, and/or performance to the any one or more of or any combination of a medication, an implement, a medical device, a treatment and a procedure that is to be provided.

8. The method of claim 7 wherein the data read from the coded wireless RFID tag includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, physician information, insurance, an illness, a disease, a condition, a name of a medication, a dosage of a medication, a frequency of administration of a medication, a prescribing person, and a condition treated.

9. The method of claim 7 wherein said comparing data from a computer database includes communicating with the computer via communication means including any one or more of wire, cable, optical fiber, local area network (LAN), wide area network (WAN), radio (RF) transmission, optical transmission, the Internet, or any combination thereof.

10. The method of claim 7 wherein the data from the computer database includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, insurance, an illness, a disease, a condition, a name of a medication, a dosage of a medication, a frequency of administration of a medication, a lot identification, an NDC number, an expiration date, a manufacturer, a prescribing person, physician information, a facility, a surgical operating room, a diagnostic machine, a dispenser, a number of refills, a condition treated, drug interaction information, allergy information, allergic reaction information, drug treatment information, drug overdose information, contraindication information, alternative treatments, expected benefits, side effects, patient information, an NDC database information, a medication database information, and inappropriate drug administration information.

11. The method of claim 7:
wherein said comparing data from a computer database includes accessing a computer relational database via communication means including any one or more of wire, cable, optical fiber, local area network (LAN), wide area network (WAN), radio transmission, optical transmission, the Internet, or any combination thereof; or said method further comprising accessing a computer relational database via communication means including any one or more of wire, cable, optical fiber, local area network (LAN), wide area network (WAN), radio transmission, optical transmission, the Internet, or any combination thereof; or both of the foregoing.

12. The method of claim 11 wherein the relational database includes any one or more of or any combination of an open database to which information can be added, deleted, and changed, a closed database not allowing information to be added, deleted or changed via the communication means, an NDC database, a medication database, and an automated diagnostic program.

13. The method of claim 11:
wherein said accessing is controlled by access codes, passwords, or both; or wherein information communicated via the communication means is encrypted; or wherein said accessing is controlled by access codes, passwords, or both, and wherein information communicated via the communication means is encrypted.

14. The method of claim 7 wherein said providing a visual indication, an audible indication, or both, includes providing at least the name of any one or more of or any combination of a medication, implement, medical device, treatment and procedure, the time at which the any one or more of or any combination of a medication, implement, medical device, treatment and procedure is to be administered or utilized.

15. The method of claim 7 further comprising providing a label associated with or affixed to the any one or more of or any combination of a medication, an implement, a medical device, a treatment and a procedure, wherein the label includes in human readable form at least a portion of the data coded in the coded wireless RFID tag.

16. A method for reducing the incidence of error in any one or more of or any combination of administering a medication, using an implement, using a medical device, administering a treatment and performing a procedure, the method comprising:

providing a coded wireless RFID tag associated with a person who is to receive any one or more of or any combination of a medication, an implement, a medical device, a treatment and a procedure;

wherein the coded wireless RFID tag includes a permanent number, coded data comprising at least an identification of the person with which it is associated and an identification of any one or more of or any combination of a medication, an implement, a medical device, a treatment and a procedure that the person is to receive, and a relational check code representative of the permanent number or of the permanent number and the coded data;

reading the coded data of the coded wireless RFID tag in conjunction with any one or more of or any combination of the administering a medication, using an implement, using a medical device, administering a treatment and performing a procedure;

processing the relational check code read from the coded wireless RFID tag for verifying the coded data read therefrom;

comparing data from a computer database that includes data corresponding to the coded data read from the coded wireless RFID tag and includes data in addition to the coded data read from the coded wireless RFID tag with the respective coded data read from the coded wireless RFID tag for matching the any one or more of or any combination of a medication, an implement, a medical device, a treatment and a procedure to be provided with the any one or more of or any combination of a medication, an implement, a medical device, a treatment and a procedure that the person is to receive; and providing, responsive to said comparing, a visual indication, an audible indication, or both, indicating whether the provided any one or more of or any combination of a medication, an implement, a medical device, a treatment and a procedure and the any one or more of or any combination of a medication, an implement, a medical device, a treatment and a procedure that the person is to receive match or do not match, whereby the person that is to receive any one or more of or any combination of a medication, an implement, a medical device, a treatment and a procedure is matched to the any one or more of or any combination of a medication, an implement, a medical device, a treatment and a procedure that is to be provided thereby reducing the likelihood of error in conjunction with administering a medication, using an implement, using a medical device, administering a treatment and performing a procedure.

17. The method of claim 16 wherein the data read from the coded wireless RFID tag includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, physician information, insurance, an illness, a disease, a condition, a name of a medication, a dosage of a medication, a frequency of administration of a medication, a prescribing person, and a condition treated.

18. The method of claim 16 wherein said comparing data from a computer database includes communicating with the computer via communication means including any one or more of wire, cable, optical fiber, local area network (LAN), wide area network (WAN), radio (RF) transmission, optical transmission, the Internet, or any combination thereof.

19. The method of claim 16 wherein the data from the computer database includes any one or more of or any combination of patient name, patient identifying information, patient identity, age, height, weight, sex, race, family and genetic data, medical history, physical handicaps, known medical conditions, known medical allergies, current ailment conditions, symptoms, duration, temperature, blood pressure, pulse rate, blood test data, urine test data, physician observations, insurance, an illness, a disease, a condition, a name of a medication, a dosage of a medication, a frequency of administration of a medication, a lot identification, an NDC number, an expiration date, a manufacturer, a prescribing person, physician information, a facility, a surgical operating room, a diagnostic machine, a dispenser, a number of refills, a condition treated, drug interaction information, allergy information, allergic reaction information, drug treatment information, drug overdose information, contraindication information, alternative treatments, expected benefits, side effects, patient information, an NDC database information, a medication database information, and inappropriate drug administration information.

20. The method of claim 16:
wherein said comparing data from a computer database includes accessing a computer relational database via communication means including any one or more of wire, cable, optical fiber, local area network (LAN), wide area network (WAN), radio transmission, optical transmission, the Internet, or any combination thereof or said method further comprising accessing a computer relational database via communication means including any one or more of wire, cable, optical fiber, local area network (LAN), wide area network (WAN), radio transmission, optical transmission, the Internet, or any combination thereof; or both of the foregoing.

21. The method of claim 20 wherein the relational database includes any one or more of or any combination of an open database to which information can be added, deleted, and changed, a closed database not allowing information to be added, deleted or changed via the communication means, an NDC database, a medication database, and an automated diagnostic program.

22. The method of claim 20:
wherein said accessing is controlled by access codes, passwords, or both; or wherein information communicated via the communication means is encrypted; or wherein said accessing is controlled by access codes, passwords, or both, and wherein information communicated via the communication means is encrypted.

23. The method of claim 16 wherein said providing a visual indication, an audible indication, or both, includes providing at least the name of any one or more of or any combination of a medication, implement, medical device, treatment and procedure, the time at which the any one or more of or any combination of a medication, implement, medical device, treatment and procedure is to be administered or utilized.

24. The method of claim 16 further comprising providing a label associated with or affixed to the any one or more of or any combination of a medication, an implement, a medical device, a treatment and a procedure, wherein the label includes in human readable form at least a portion of the data coded in the coded wireless RFID tag.

* * * * *